United States Patent
Togino

(10) Patent No.: US 8,289,630 B2
(45) Date of Patent: *Oct. 16, 2012

(54) OPTICAL ELEMENT, OPTICAL SYSTEM HAVING THE SAME AND ENDOSCOPE USING THE SAME

(75) Inventor: Takayoshi Togino, Koganci (JP)

(73) Assignee: Olympus Corporation, Tokyo (JP)

( * ) Notice: Subject to any disclaimer, the term of this patent is extended or adjusted under 35 U.S.C. 154(b) by 362 days.

This patent is subject to a terminal disclaimer.

(21) Appl. No.: 12/655,908

(22) Filed: Jan. 7, 2010

(65) Prior Publication Data

US 2010/0110565 A1 May 6, 2010

Related U.S. Application Data

(63) Continuation of application No. PCT/JP2008/062652, filed on Jul. 8, 2008.

(30) Foreign Application Priority Data

Jul. 9, 2007 (JP) ................................ 2007-180149

(51) Int. Cl.
G02B 17/00 (2006.01)

(52) U.S. Cl. .......................... 359/726; 359/729; 359/731

(58) Field of Classification Search ........... 359/726–736
See application file for complete search history.

(56) References Cited

U.S. PATENT DOCUMENTS

| | | | |
|---|---|---|---|
| 3,505,465 A | 4/1970 | Rees | |
| 5,854,713 A | 12/1998 | Kuroda et al. | |
| 6,115,193 A | 9/2000 | Shu | |
| 6,175,454 B1 | 1/2001 | Hoogland et al. | |
| 6,356,296 B1 | 3/2002 | Driscoll, Jr. et al. | |
| 6,392,687 B1 | 5/2002 | Driscoll, Jr. et al. | |
| 6,449,103 B1 | 9/2002 | Charles | |
| 6,597,520 B2 | 7/2003 | Wallerstein et al. | |
| 7,929,219 B2 * | 4/2011 | Togino | 359/736 |
| 2004/0254424 A1 | 12/2004 | Simkulet et al. | |
| 2010/0110564 A1 * | 5/2010 | Togino | 359/725 |

FOREIGN PATENT DOCUMENTS

| | | |
|---|---|---|
| JP | 60-42728 | 3/1985 |
| JP | 2001-174713 | 6/2001 |
| JP | 2002-341409 | 11/2002 |
| JP | 2003-167193 | 6/2003 |
| JP | 2005-148265 | 6/2005 |
| JP | 2006-058412 | 3/2006 |
| JP | 2006-276816 | 10/2006 |
| WO | WO 03-042743 | 5/2003 |

* cited by examiner

*Primary Examiner* — Scott J Sugarman
(74) *Attorney, Agent, or Firm* — Kenyon & Kenyon LLP

(57) ABSTRACT

An optical element that is made of a transparent medium L1 rotationally symmetric relative to the central axis 2 with a refractive index greater than 1, wherein the transparent medium L1 has a first transmissive surface 11, a first reflective surface 12, a second reflective surface 13 arranged at an opposite side to the image plane 5 relative to the first reflective surface 12 and a second transmissive surface 14 arranged at the image plane 5 side relative to the second reflective surface 13 and that the flux of light entering the transparent medium L1 goes into it by way of the first transmissive surface 11 so as to be reflected to the opposite side to the image plane 5 by the first reflective surface 12 and then to the image plane 5 side by the second reflective surface 13 to form an optical path before going out from the transparent medium L1 at the image plane 5 side by way of the second transmissive surface 14 in the order of forward ray tracing.

21 Claims, 20 Drawing Sheets

FIG. 15
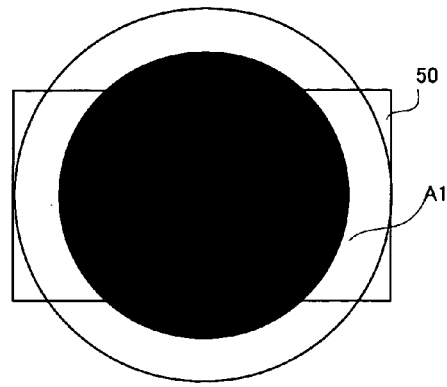
(a)
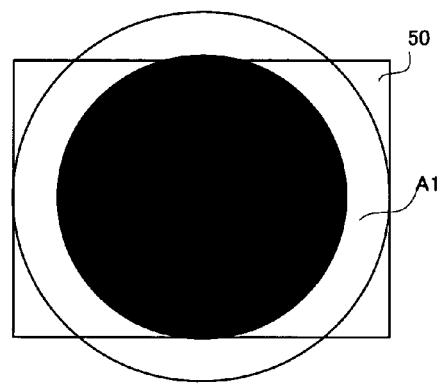
(b)
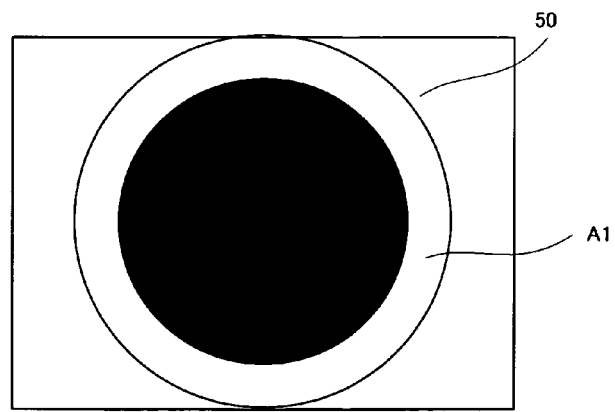
(c)

FIG. 18
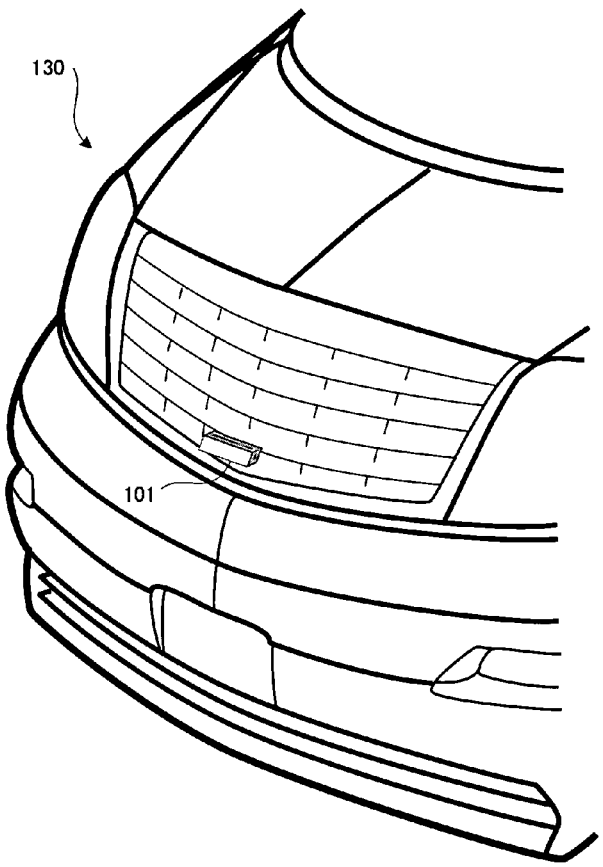
(a)
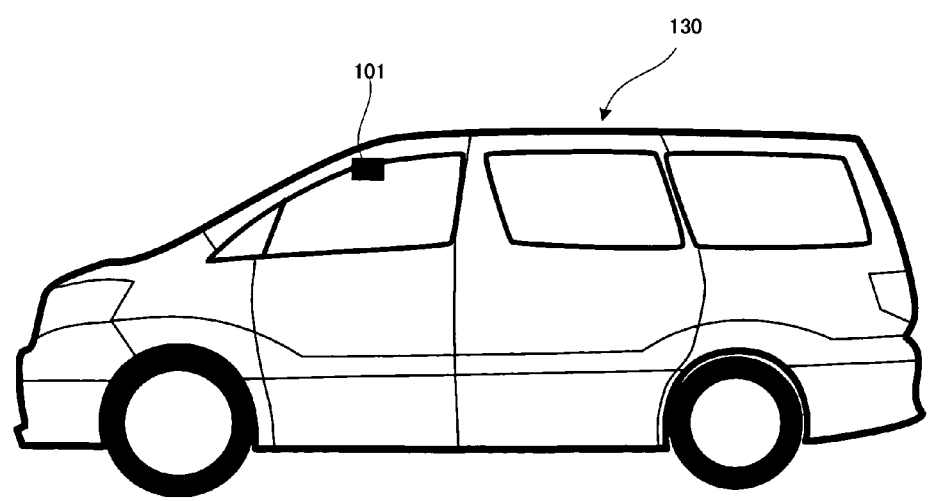
(b)

OPTICAL ELEMENT, OPTICAL SYSTEM HAVING THE SAME AND ENDOSCOPE USING THE SAME

This application is a continuation of PCT International Application No. PCT/JP 2008/062652 filed on Jul. 8, 2008, which designates the United States. A claim of priority and the benefit of the filing date under 35 U.S.C. §120 is hereby made to PCT International Application No. PCT/JP2008/062652 filed on Jul. 8, 2008, which in turn claims priority under 35 U.S.C. §119 to Japanese Application No. 2007-180149 filed on Jul. 9, 2007, each of which is expressly incorporated herein in its entirety by reference thereto.

BACKGROUND OF THE INVENTION AND RELATED ART STATEMENT

The present invention relates to an optical element, an optical system having such an optical element and an endoscope using such an optical system. More particularly, the present invention relates to an image formation optical system or a projection optical system having a function of forming an image around an axis of rotational symmetry as an annular image to an image pickup device.

Patent Document 1 listed below describes a known image pickup optical system having a refraction optical system, a reflection optical system and an image formation optical system arranged therein along with two optical paths so as to be capable of picking up a panoramic image and an axial image. Patent Document 2 describes a known endoscope similarly having two optical paths. Further, Patent Document 3 describes a known endoscope by means of which it is possible to omni-directionally observe the surroundings and Patent Document 4 describes a known capsule endoscope by means of which it is also possible to omni-directionally observe the surroundings. Furthermore, Patent Document 5 describes an image pickup device that can shoot omni-directionally the surroundings and also only forward at the same time. Finally, Patent Documents 6 through 13 describe an omni-directional optical system.

[Patent Document 1] Jpn. PCT National Publication No. 2003-042743
[Patent Document 2] U.S. Patent Application Publication No. 2004-0254424
[Patent Document 3] JP-A-60-42728
[Patent Document 4] JP-A-2001-174713
[Patent Document 5] JP-A-2002-341409
[Patent Document 6] U.S. Pat. No. 3,505,465
[Patent Document 7] U.S. Pat. No. 5,854,713
[Patent Document 8] U.S. Pat. No. 6,115,193
[Patent Document 9] U.S. Pat. No. 6,175,454
[Patent Document 10] U.S. Pat. No. 6,356,296
[Patent Document 11] U.S. Pat. No. 6,392,687
[Patent Document 12] U.S. Pat. No. 6,449,103
[Patent Document 13] U.S. Pat. No. 6,597,520

SUMMARY OF THE INVENTION

An aspect of the present invention provides an optical element that is made of a transparent medium rotationally symmetric relative to the central axis with a refractive index greater than 1, where in the transparent medium has a first transmissive surface, a first reflective surface, a second reflective surface arranged at an opposite side to the image plane relative to the first reflective surface and a second transmissive surface arranged at the image plane side relative to the second reflective surface and the flux of light entering the transparent medium goes into it by way of the first transmissive surface so as to be reflected to the opposite side to the image plane by the first reflective surface and then to the image plane side by the second reflective surface to form an optical path before going out from the transparent medium at the image plane side by way of the second transmissive surface in the order of forward ray tracing.

Preferably, the optical path is formed a substantially Z-shaped optical path.

Preferably, the optical path is formed only at a side relative to the central axis.

Preferably, the second transmissive surface is arranged near the central axis and the first reflective surface and the second reflective surface are arranged in a peripheral part thereof, while the first transmissive surface is arranged at the outermost periphery thereof.

Preferably, each of the first reflective surface and the second reflective surface is formed by a toric surface.

Preferably, at least either the first reflective surface and the second reflective surface has a total reflection effect.

Preferably, at least either the first reflective surface and the second reflective surface is formed by an extended rotary free curved surface formed by rotating a line segment of arbitrary shape having no plane of symmetry around the central axis.

Preferably, at least one of the surfaces that the transparent medium has is formed by an extended rotary free curved surface formed by rotating a line segment of arbitrary shape including one or more than one odd-number-th degree terms.

Another aspect of the present invention provides an optical system having an optical element according to the present invention, where in the system includes a front group, a back group arranged at the image plane side relative to the front group and an aperture arranged between the front group and the back group and that the optical element is arranged in the front group to form an image of an object arranged so as to surround the central axis or project an image of the object in a radial direction from the central axis.

Preferably, the optical system as defined above forms an image of an annular object around the central axis in a plane orthogonal relative to the central axis.

Preferably, the second reflective surface is arranged with its concave surface directed to the aperture.

Preferably, the second transmissive surface is arranged with its concave surface directed to the aperture.

Preferably, the optical system as defined above does not form any intermediate image on the optical path.

Preferably, the optical system as defined above satisfies the condition of $$1 < d/t \quad (1),$$

where t is the thickness of the optical element as measured in the direction of the axis of rotational symmetry and d is the external dimension of the optical element.

More preferably, the optical system as defined above further satisfies the condition of $$3 < d/t \quad (1\text{-}1),$$

where t is the thickness of the optical element as measured in the direction of the axis of rotational symmetry and d is the external dimension of the optical element.

Preferably, the optical system as defined above further satisfies the condition of $$20 < \theta 2 < 40$$

where θ1 is the angle of incidence of the central principal ray of light on the first reflective surface and θ2 is the angle of incidence of the central principal ray of light on the first reflective surface of the optical element.

Preferably, the first reflective surface is arranged at the opposite side to the image plane relative to the aperture.

Preferably, the optical system as defined above further satisfies the condition of $$0 < d1/ts < 1 \qquad (3),$$

where ts is the length of the gap between the first reflective surface and the aperture and d1 is the diameter of the first reflective surface of the optical element.

Preferably, the optical system as defined above further satisfies the condition of $$0.05 < \beta < 2 \qquad (4),$$

where β is the angular magnification of the view angle of the meridional cross section.

More preferably, the optical system as defined above further satisfies the condition of $$0.1 < \beta < 2 \qquad (4\text{-}1),$$

where β is the angular magnification of the view angle of the meridional cross section.

Another aspect of the present invention provides an endoscope formed by using an optical system as defined above.

BRIEF DESCRIPTION OF THE DRAWINGS

FIG. 15 is a schematic illustration of an exemplar positional arrangement of the image and the imaging element of an optical system according to the present invention.

FIG. 18 is a schematic illustration of examples of using an optical system according to the present invention as an image pickup optical system of an automobile.

DETAILED DESCRIPTION OF PREFERRED EMBODIMENTS

Now, an optical element and an optical system including such an optical element according to the present invention will be described below based on examples.

Figure 3:
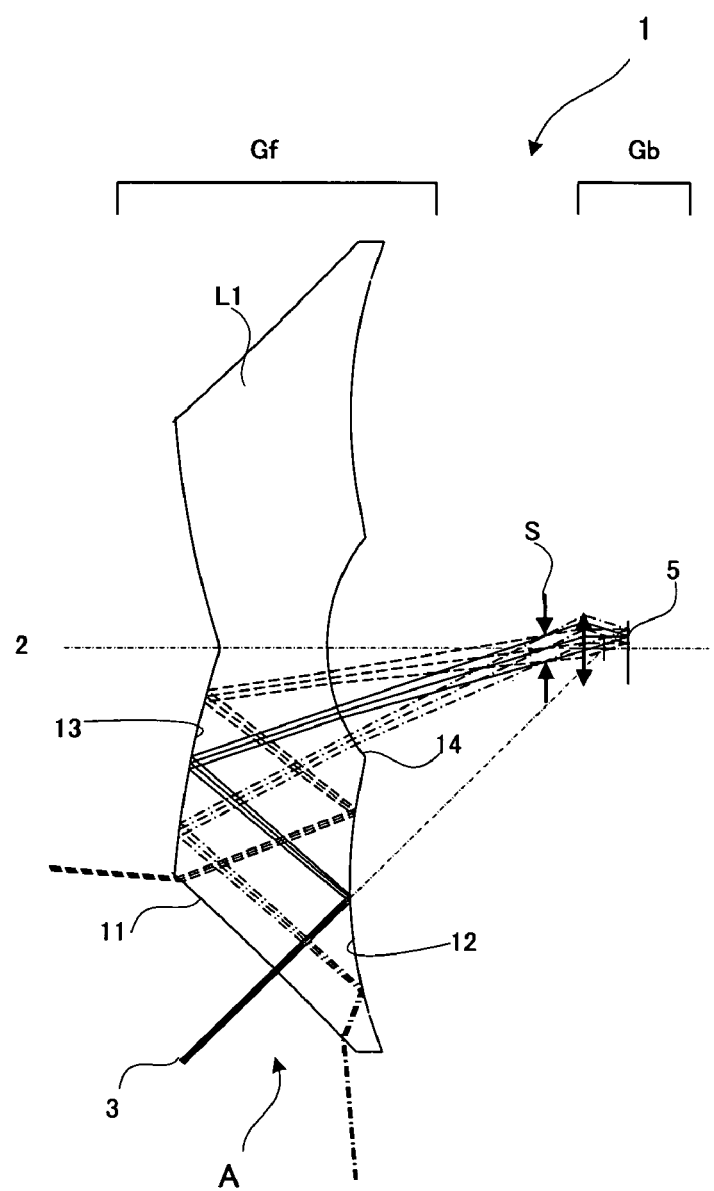
FIG. 3 is a schematic cross-sectional view of the optical system of Example 1 of the present invention taken along the central axis thereof.

FIG. 3 is a schematic cross-sectional view of the optical system 1 of Example 1 of the present invention, which will be described in greater detail hereinafter, taken along the central axis (axis of rotational symmetry) 2 thereof. Note that, while the optical system is described below in terms of image formation optical system, it is also applicable to a projection optical system by using the optical path reversely.

The optical system 1 of Example 1 includes a front group Gf that is rotationally symmetric relative to a central axis 2 and has negative power, an aperture S and a back group Gb having positive power and can form or project an image without forming an intermediate image on any optical path. The back group Gb of this example is an ideal lens.

Thus, the embodiment of the present invention provides a compact optical system having a simple configuration and excellent resolving power for which aberrations are corrected satisfactorily and that can observe or project an image in different directions.

Therefore, the embodiment of the present invention provides a compact and inexpensive optical element that has a simple configuration and can form an omni-directional image in a direction substantially orthogonal to the central axis on a single imaging element with little image distortions and high resolving power to represent an excellent F-θ characteristic, an optical system having such an optical element and also an endoscope formed by using such an optical system.

The optical system becomes of a so-called retro-focus type when the front group Gf is made negative and the back group Gb is made positive. Such an arrangement is effective particularly when a wide view angle needs to be secured.

An optical element according to the present invention is made of a transparent medium L1 rotationally symmetric relative to the central axis 2 with a refractive index greater than 1 and the transparent medium L1 has a first transmissive surface 11, a first reflective surface 12, a second reflective surface 13 arranged at the opposite side to the image plane 5 relative to the first reflective surface 12 and a second transmissive surface 14 arranged at the image plane 5 side relative to the second reflective surface 13. The flux of light entering the transparent medium L1 goes into the transparent medium L1 by way of the first transmissive surface 11 so as to be reflected to the opposite side to the image plane 5 by the first reflective surface 12 and then to the image plane 5 side by the second reflective surface 13 to form a substantially Z-shaped optical path A before going out from the transparent medium L1 at the image plane 5 side by way of the second transmissive surface 14 in the order of forward ray tracing.

With the above-described arrangement, the angle of incidence relative to the first reflective surface 12 and the second reflective surface 13 of the optical path A can be made relatively small to minimize the eccentric aberration that arises at each of the reflective surfaces.

Additionally, the optical path does not cross the central axis 2 in the optical element to make it possible to reduce the thickness of the optical element as the optical path A is arranged only at a side of the central axis.

Still additionally, the optical path A can be made to enter the optical element in a direction substantially orthogonal to the central axis 2 and pass through the second transmissive surface 14 after being reflected by the first reflective surface 12 and the second reflective surface 13 when the second transmissive surface 14 is arranged in the vicinity of the central axis 2 and the first reflective surface 12 and the second reflective surface 13 are arranged in a peripheral part thereof, while the first transmissive surface 11 is arranged in the outermost peripheral part thereof. Then, the first reflective surface 11(12?) and the second reflective surface 13 can be arranged as internal reflective surfaces. Thus, it is possible to minimize the eccentric aberration by using internal reflective surfaces.

Still Additionally, the distortions at and near the view angle can be minimized because each of the first reflective surface 12 and the second reflective surface 13 is formed by using a toric surface.

Still additionally, no reflective surface needs to be provided to facilitate the preparation of an optical element according to the present invention when the first reflective surface 12 and/or the second reflective surface 13 are made to have a total reflection effect. Then, the reflectivity can be made equal to 100% at the same time to make it possible to pick up a bright image.

Still additionally, the distortions at and near the view angle can be corrected when at least either the first reflective surface 12 and the second reflective surface 13 is formed by an extended rotary free curved surface formed by rotating a line segment of arbitrary shape having no plane of symmetry around the central axis 2.

Still additionally, an optical element according to the present invention can be made to have a shape that is vertically asymmetric relative to the center of the view angle to make it advantageous for correcting aberrations when at least one of the surfaces that the transparent medium L1 has is formed by an extended rotary free curved surface formed by rotating a line segment of arbitrary shape including one or more than one odd-number-th degree terms around the central axis 2.

Preferably, both of the two reflective surfaces having a reflection effect are so arranged that the concave surfaces thereof are directed to the aperture S. Then, as a result, the reflective surfaces represent a negative-positive power arrangement to make the power arrangement of the reflective surfaces of the optical element itself a retro-focus type so that it can take a wide view angle with ease and comatic aberration hardly arises there.

Preferably, the second transmissive surface is a surface having strong negative power with its concave surface directed to the aperture side. The view angle of the ray of light entering the back group can be reduced to by turn reduce the load of correcting the aberrations of the back group. It is possible to realize a compact optical system with a small number of constituent surfaces by reducing the view angle of the ray of light passing through the surface and going out from the optical element.

Additionally, the front group and the back group are made well balanced to produce a favorable effect for downsizing and simplifying the optical system by arranging the optical element close to the object relative to the aperture. It is hardly possible to achieve a large angular magnification and the load of the other lenses is raised when the optical element is arranged near the aperture because the central ray of light of a meridional cross section and a ray of light having a large view angle are found close to each other in the vicinity of the aperture. Additionally, it is difficult to provide a wide view angle for the front group located at the object side relative to the aperture when the optical element is arranged at the image side of the aperture.

Since the optical system does not form any intermediate image in the optical path, it is possible to reduce the overall length of the optical system. Then, it is possible to by turn downsize the optical system.

Preferably, the optical system satisfies the condition of $$1 < d/t \qquad (1),$$

where t is the thickness of the optical element as measured in the direction of the axis of rotational symmetry and d is the external dimension of the optical element.

The conditional formula (1) provides a condition for the optical system to be downsized. The overall size of the image forming optical system arranged at the image side relative to the optical element becomes too large when d/t falls below the above lower limit.

More preferably, the optical system satisfies the condition of $$3 < d/t \qquad (1\text{-}1),$$

where t is the thickness of the optical element as measured in the direction of the axis of rotational symmetry and d is the external of dimension of the optical element. Then, the optical system can be further downsized.

Preferably, the optical system satisfies the condition of $$20 < \theta 2 < 40 \qquad (2),$$

where $\theta 1$ is the angle of incidence of the central principal ray of light on the first reflective surface and $\theta 2$ is the angle of incidence of the central principal ray of light on the first reflective surface of the optical element.

When $\theta 2$ falls below the lower limit of the conditional formula (2), the angle of incidence at the second reflective surface 13 becomes too small to make it no longer possible to arrange the first reflective surface 12 and the second transmissive surface 14 side by side and secure a wide view angle in the vertical direction and inevitably bring the first reflective surface 12 too close to the axis of rotational symmetry so that the curve of the sagittal image plane becomes too large and a large sagittal comatic aberration takes place to make it impossible for the other surfaces to correct these problems.

When $\theta 2$ exceeds the upper limit of the conditional formula (2), the optical system becomes large and, at the same time, the eccentric aberration that takes place at the second reflective surface 13 becomes too large to be corrected by using one or more than one odd-number-th degree terms.

Still preferably, the first reflective surface 12 is arranged at the opposite side to the image plane 5 relative to the aperture S that operates as a stop. This is an important condition to be satisfied for avoiding the interference of the lens of the back group Gb and the first reflective surface 12. The optical system of the back group Gb or some other arbitral image forming optical system and the first reflective surface 12 interfere with each other when the first reflective surface 12 is arranged at the image plane 5 side relative to the aperture stop S. Then, the first reflective surface 12 inevitably needs to become large and, as a result, the entire optical system becomes large. No interference arises between the first reflective surface 12 and the image forming optical system when the first reflective surface 12 is arranged at the opposite side to the image plane 5 relative to the aperture stop S.

Preferably, the optical system further satisfies the condition of $$0 < d1/ts < 1 \quad (3),$$

where ts is the length of the gap between the first reflective surface and the aperture and d1 is the diameter of the first reflective surface of the optical element.

The explanation of the lower limit of the conditional formula (1) also applies to the lower limit of this conditional formula (3). The aperture stop is located far from the optical element of the present invention when the ratio of d1/ts exceeds the upper limit of the conditional formula (3). Then, as a result, an image forming optical system having a relatively long focal length is required to consequently make the imaging optical system and hence the overall optical system large so that it is no longer possible to provide an optical system that can produce bright images.

Preferably, the optical system satisfies the condition of $$0.05 < \beta < 2 \quad (4),$$

where β is the angular magnification of the view angle of the meridional cross section.

The value of β will be too small when it falls below the lower limit of the conditional formula (4). Then, the angular magnification for reduction of the optical element of the present invention becomes too small so that the load of the optical element of the present invention increases too much to produce any favorable result. Additionally, an optical system having a long focal distance will be required, although the view angle of the back group may be small. The optical system of a back group having a long focal length and a small F number that can produce bright images tends to become large to a great disadvantage for downsizing the optical system.

The view angle of the back group needs to be large and the focal length of the back group becomes too short when β exceeds the upper limit of the conditional formula (4). Then, the load of the back group for the view angle becomes disadvantageously too large.

More preferably, the optical system satisfies the condition of $$0.1 < \beta < 2 \quad (4\text{-}1),$$

where β is the angular magnification of the view angle of the meridional cross section.

Now, Examples 1 through 4 of optical system according to the present invention will be described below. The parameters of the optical systems of these examples will be described hereinafter.

Figure 1:
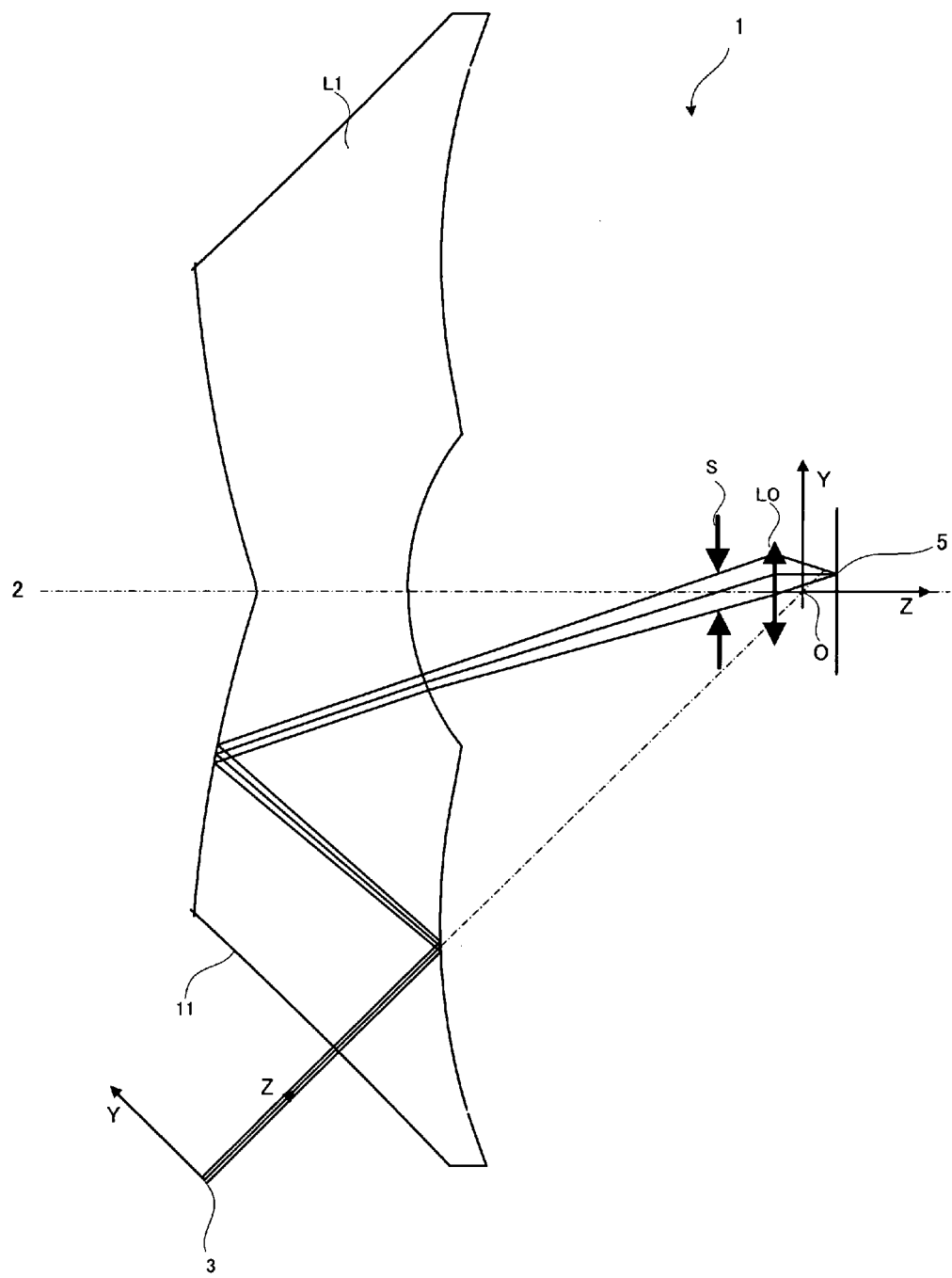
FIG. 1 is a schematic illustration of the coordinate system of an optical system according to the present invention.

As coordinate system in forward ray tracing, for instance, the point of intersection of a prolonged line of the central principal ray of light proceeding from the object surface 3 toward the first surface and the central axis 2 is taken as origin O of eccentric optical surface and the direction orthogonal to the central axis 2 and of moving toward the opposite side to the object surface 3 as viewed from the central axis 2 is taken as a Y-axis positive direction as illustrated in FIG. 1, whereas the surface plane of the sheet of FIG. 1 is taken as a Y-Z plane. Then, the direction of moving toward the image plane 5 in FIG. 1 is taken as a Z-axis positive direction and the axis that constitutes a right hand orthogonal coordinate system with the Y-axis and the Z-axis is taken as an X-axis positive direction.

As for the eccentric surface, the eccentricity from the origin O of the above optical system 1 that is used for defining the coordinate system that by turn defines the surface (as expressed by X, Y and Z respectively in the X-axis direction, the Y-axis direction and the Z-axis direction) and the angles of inclination of the planes extending respectively through the X-axis, the Y-axis and the Z-axis in the coordinate system that is defined by using the origin O of the optical system 1 (α, β and γ (°) respectively) are given. Note that α and β are taken as positive respectively in the counterclockwise directions relative to the positive direction of the X-axis and that of the Y-axis and γ is taken as positive in the clockwise direction relative to the position direction of the Z-axis. Also note that each of the planes is rotated around the central axis thereof by α, β and γ in such a way that the coordinate system that defines the planes is rotated firstly counterclockwise by α around the X-axis of the coordinate system that is defined by using the origin of the optical system and then the coordinate system obtained by rotating the initial coordinate system is rotated counterclockwise by β around the Y-axis thereof. Then, finally, the coordinate system obtained by rotating the second coordinate system is rotated clockwise by γ around the Z-axis thereof.

When a specific plane and the subsequent plane of the optical acting planes that the optical system of each of the examples includes form a coaxial optical system, the plane gap is given. Otherwise, the radius of curvature of each plane, the refractive index of the medium and the Abbe number are given according to the common practice.

All the terms relating to aspheric planes that are not described in the data on the constituent parameters that will be described hereinafter are equal to 0. The refractive index and the Abbe number relative to d-lines (wavelength: 587.56 nm) are given. The unit of length is mm. The eccentricity of each plane is expressed by the eccentricity from the reference plane as described above.

An aspheric plane is a rotationally symmetric defined by the formula represented below.

$$Z = (Y^2/R)/[1+\{1-(1+k)Y^2/R^2\}^{1/2}] + aY^4 + bY^6 + cY^8 + dY^{10} + \ldots \quad (a)$$

provided that Z is selected as an axis and Y denotes a direction perpendicular to the axis. In the above formula, R is the near-axis radius of curvature, k is the conic constant and a, b, c, d, . . . are respectively the aspheric surface coefficients of the fourth degree, the sixth degree, the eighth degree, the tenth degree and so on. The Z-axis of the above defining formula operates as the axis of a rotationally symmetric aspheric surface.

An extended rotary free curved surface is a rotationally symmetric surface given by the following definition.

Figure 2:
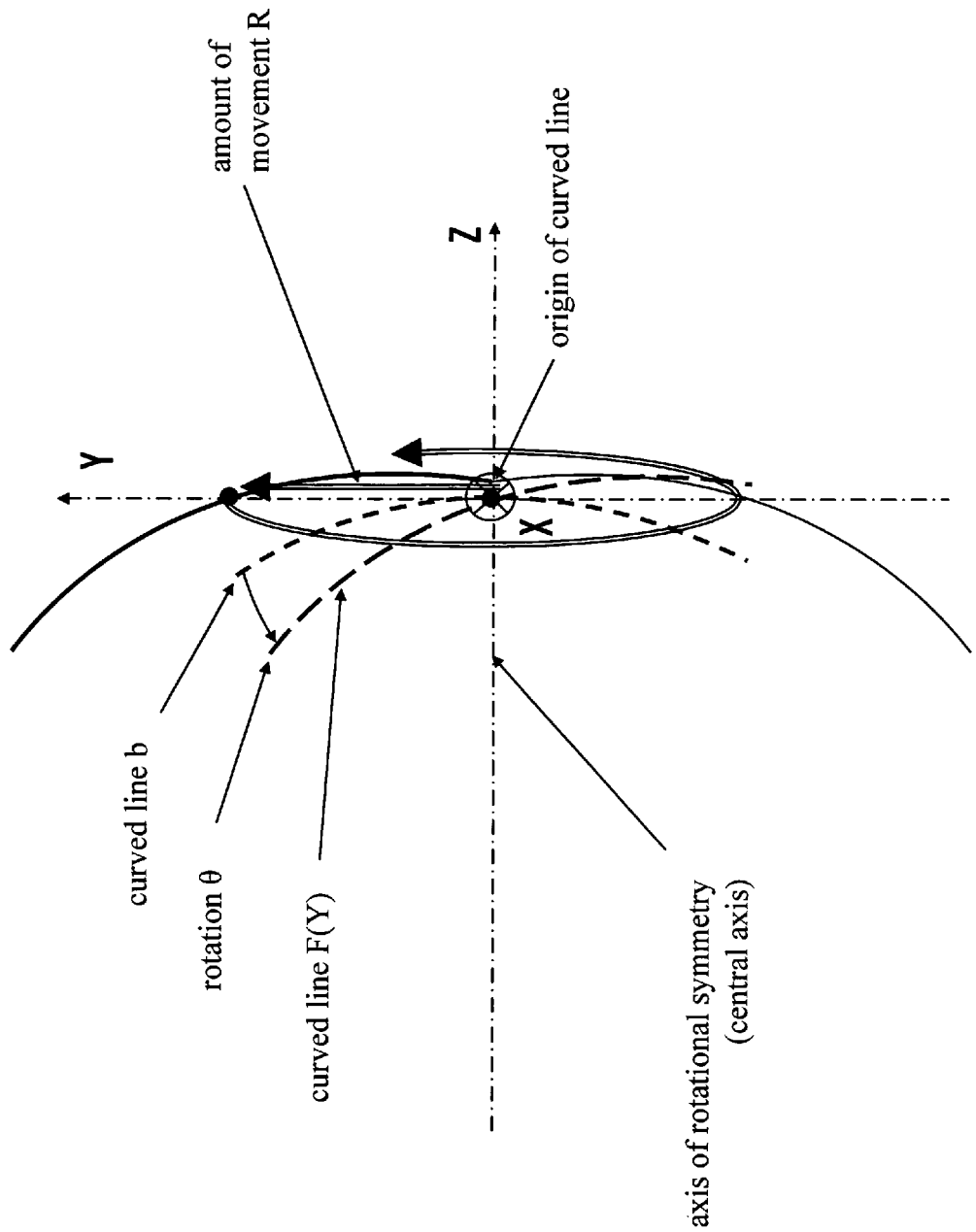
FIG. 2 is a schematic illustration of the principle of extended rotary free curved surfaces.

Firstly, a curved line (b) that passes through the origin on the Y-Z coordinate plane as illustrated in FIG. 2 is defined.

$$Z = (Y^2/RY)/[1+\{1-(C_1+1)Y^2/RY^2\}^{1/2}] + C_2Y + C_3Y^2 + C_4Y^3 + C_5Y^4 + C_6Y^5 + C_7Y^6 + \ldots + C_{21}Y^{20} + \ldots + C_{n+1}Y^n + \ldots \quad (b)$$

Then, curbed line F(Y) is defined by rotating the curbed line (b) by angle θ(°), which is positive when it is rotated counterclockwise, facing in the positive direction of the X-axis. The curved line F(Y) also passes through the origin on the Y-Z coordinate plane.

The curved line F(Y) is translated in the direction of the positive direction of the Y-axis by distance R (in the negative direction of the Y-axis when it represents a negative value)

and subsequently the translated curved line is rotated around the Z-axis to form a rotationally symmetric surface, which is an extended rotary free curved surface.

Then, as a result, the extended rotary free curved surface produces a free curved surface (free curved line) in the Y-Z plane and a circle of radius |R| in the X-Y plane.

From the above definition, the Z-axis operates as the axis (the axis of rotational symmetry) of the extended rotary free curved surface.

In the above formula (b), RY is the radius of curvature of the sphere term in the Y-Z cross section, $C_1$ is the conic constant and $C_2, C_3, C_4, C_5, \ldots$ are respectively the aspheric coefficients of the first degree, the second degree, the third degree, the fourth degree and so on.

Note that a surface of circular cone whose central axis is parallel to the Z-axis is given as an extended rotary free curved surface with RY=∞, $C_1, C_2, C_3, C_4, C_5, \ldots = 0$, θ=(the angle of inclination of the surface of circular cone) and R=(the radius of the bottom in the X-Z plane).

All the terms relating to aspheric planes that are not described in the data on the constituent parameters that will be described hereinafter are equal to 0. The refractive index and the Abbe number relative to d-lines (wavelength: 587.56 nm) are given. The unit of length is mm. The eccentricity of each plane is expressed by the eccentricity from the reference plane as described above.

Figure 4:
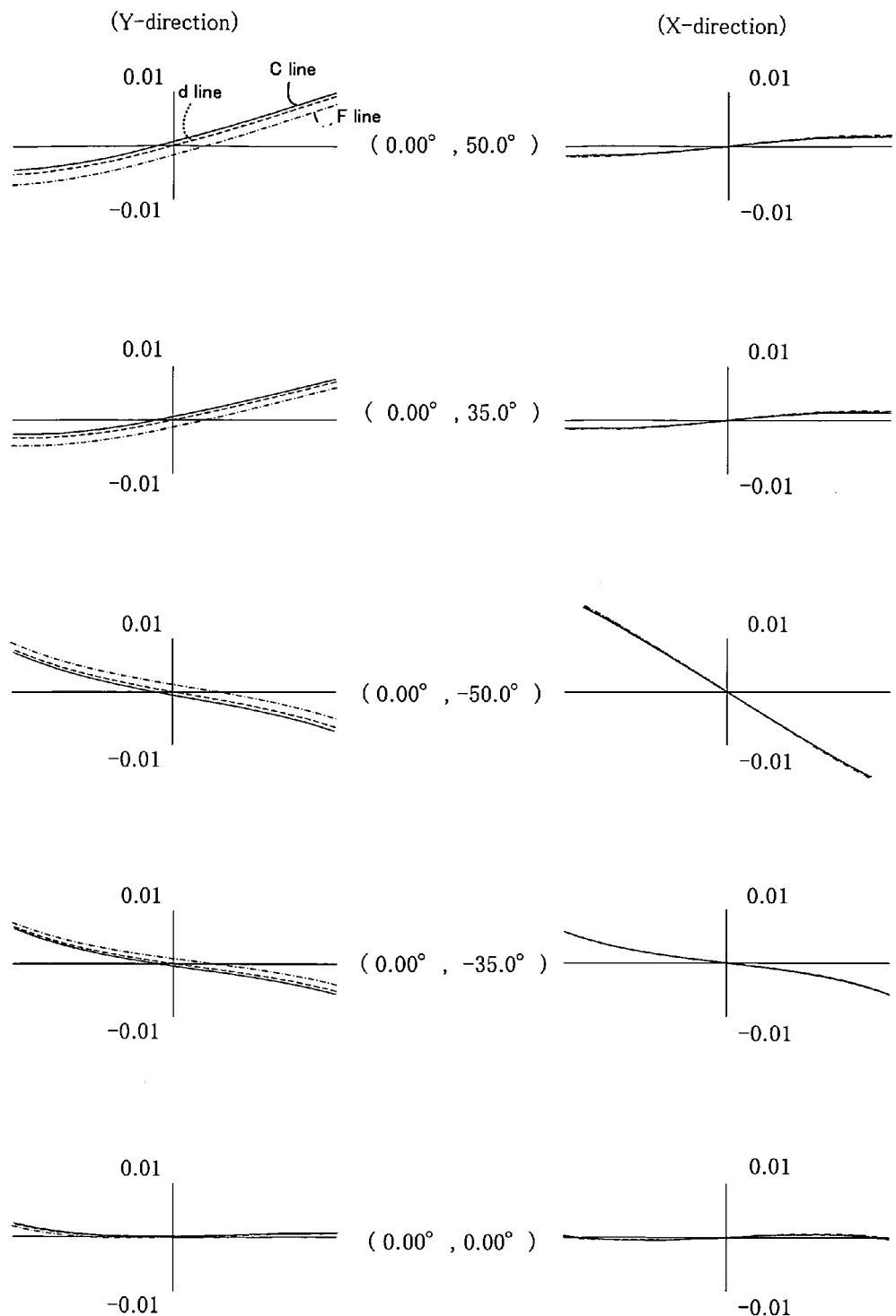
FIG. 4 is a schematic illustration of the transverse aberrations of the overall optical system of Example 1.
Figure 5:
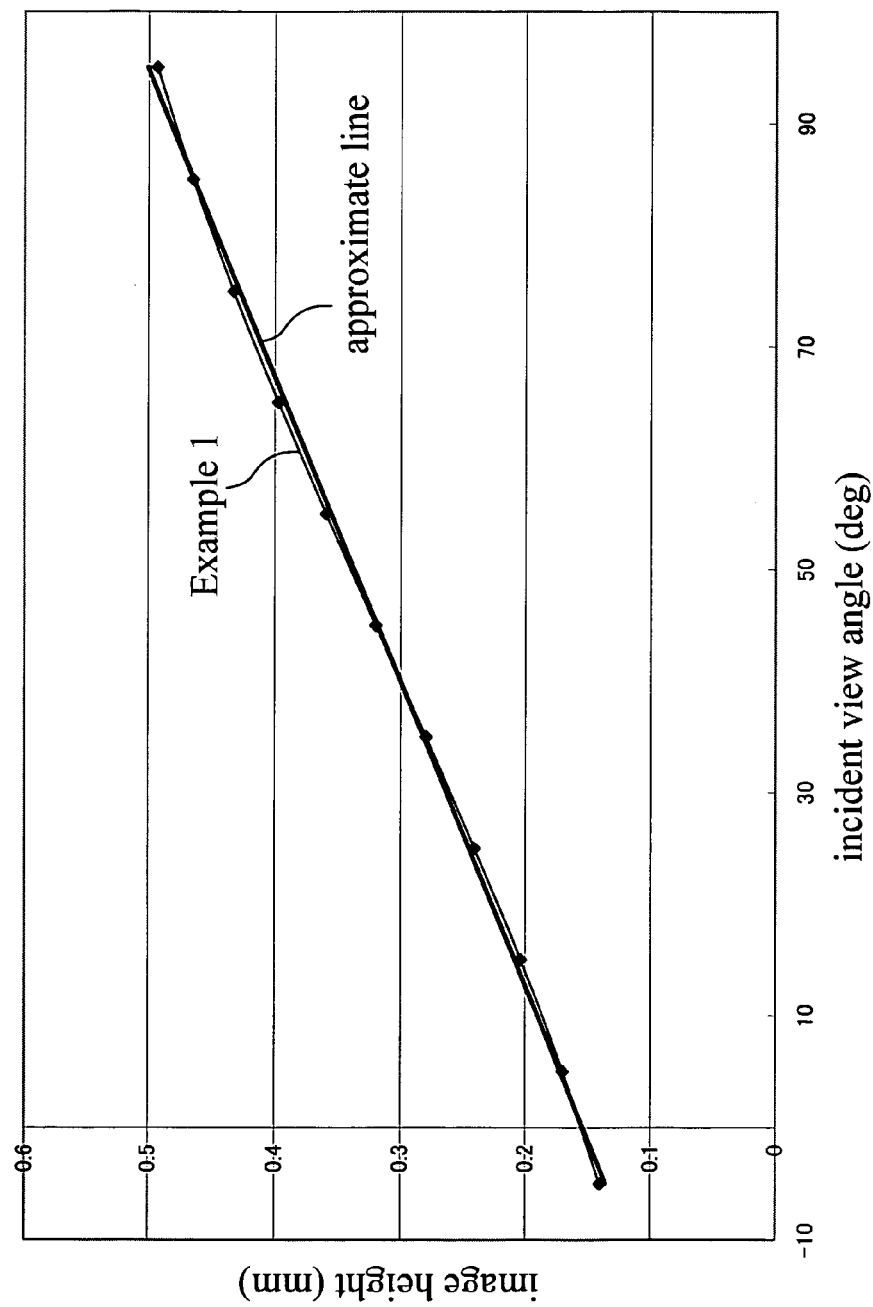
FIG. 5 is an F-θ graph of the overall optical system of Example 1.

FIG. 3 is a schematic cross-sectional view of the optical system 1 of Example 1 taken along the central axis 2 thereof. FIG. 4 is a schematic illustration of the transverse aberrations of the overall optical system of this example on the side view optical path thereof. FIG. 5 is a graph indicating the relationship between the view angle and the image height (F-G diagram). In each of the views representing the transverse aberrations, each pair of angle values represented at the center indicates (the view angle in the horizontal direction, the view angle in the vertical direction). The transverse aberrations in the Y-direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, none of the transmissive surfaces and the reflective surfaces of the transparent medium, which is concentric with and rotationally symmetric relative to the central axis of the optical system 1 and has a refractive index greater than 1, is shared in the optical path and hence all the surfaces are different surfaces. The optical system is formed as an attachment optical system to be fitted to the front end of an existing optical system. In the drawings, the arrows indicate an ideal lens L0.

The optical system 1 includes a front group Gf that is rotationally symmetric relative to the central axis 2, a back group Gb that is made of an ideal lens L0 and an aperture S arranged between the front group Gf and the back group Gb so as to be coaxial with the central axis 2.

The front group Gf is formed by a transparent medium L1 that is rotationally symmetric relative to the central axis 2 and has a refractive index greater than 1. The transparent medium L1 has a first transmissive surface 11 that is arranged vis-a-vis the object surface and formed by a toric surface at the external side relative to the central axis 2, a first reflective surface 12 that is formed by a toric surface in the inside of the transparent medium L1 and has negative power, a second reflective surface 13 that is formed by a toric surface in the inside of the transparent medium L2 at the opposite side to the image plane 5 relative to the first reflective surface 12 and has positive power and a second transmissive surface 14 that is formed by a spherical surface at the image plane 5 side relative to the second reflective surface 13 and has negative power.

The back group Gb is an ideal lens L0.

The optical system 1 forms an optical path A. As for the optical path A, the flux of light entering it from the object surface 3 of the optical system 1 proceeds sequentially by way of the front group Gf and the back group Gb and forms an annular image off the central axis 2 of the image plane 5 extending perpendicularly relative to the central axis 2.

The flux of light entering the optical system 1 to proceed along the optical path A goes into the transparent medium L1 of the front group Gf by way of the first transmissive surface 11 so as to be reflected by the first reflective surface 12 to the opposite side to the image plane 5 and then by the second reflective surface 13 to the image plane 5 side to form a subsequently Z-shaped optical path before going out from the transparent medium L1 by way of the second transmissive surface 14.

Subsequently, the flux of light proceeds by way of the aperture S that is arranged between the front group Gf and the back group Gb coaxially with the central axis 2 to operate as a stop and the ideal lens L0 of the back group Gb to form an image at a radially predetermined position off the central axis 2 of the image plane 5.

The specifications of Example 1 are as follows.

| view angle | −5° to 95° |
|---|---|
| image size | ø0.28 to ø0.99 |
| F number | 1.78 |
| f of ideal lens | 1.00 |

Figure 6:
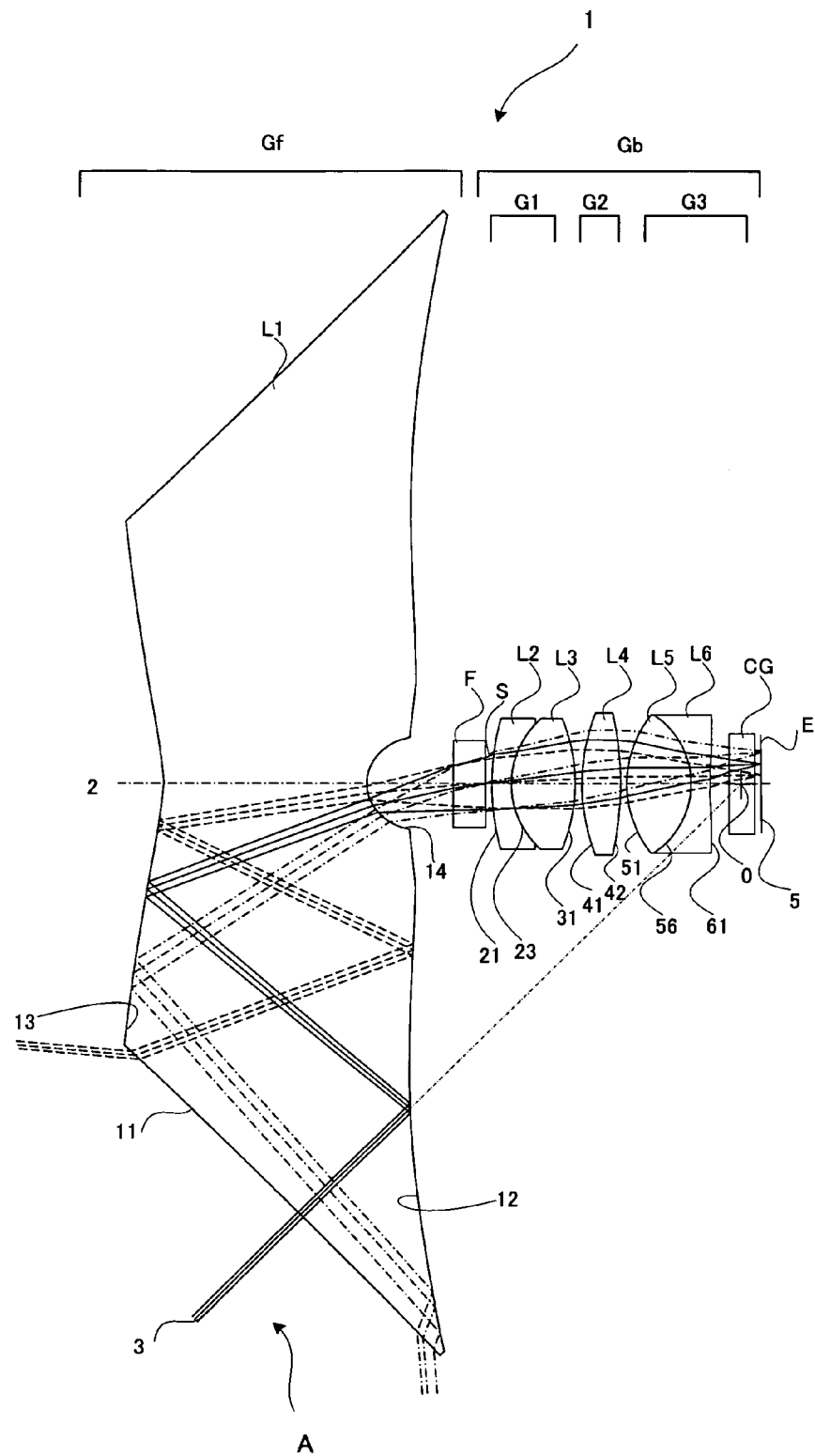
FIG. 6 is a schematic cross-sectional view of the optical system of Example 2 of the present invention taken along the central axis thereof.
Figure 7:
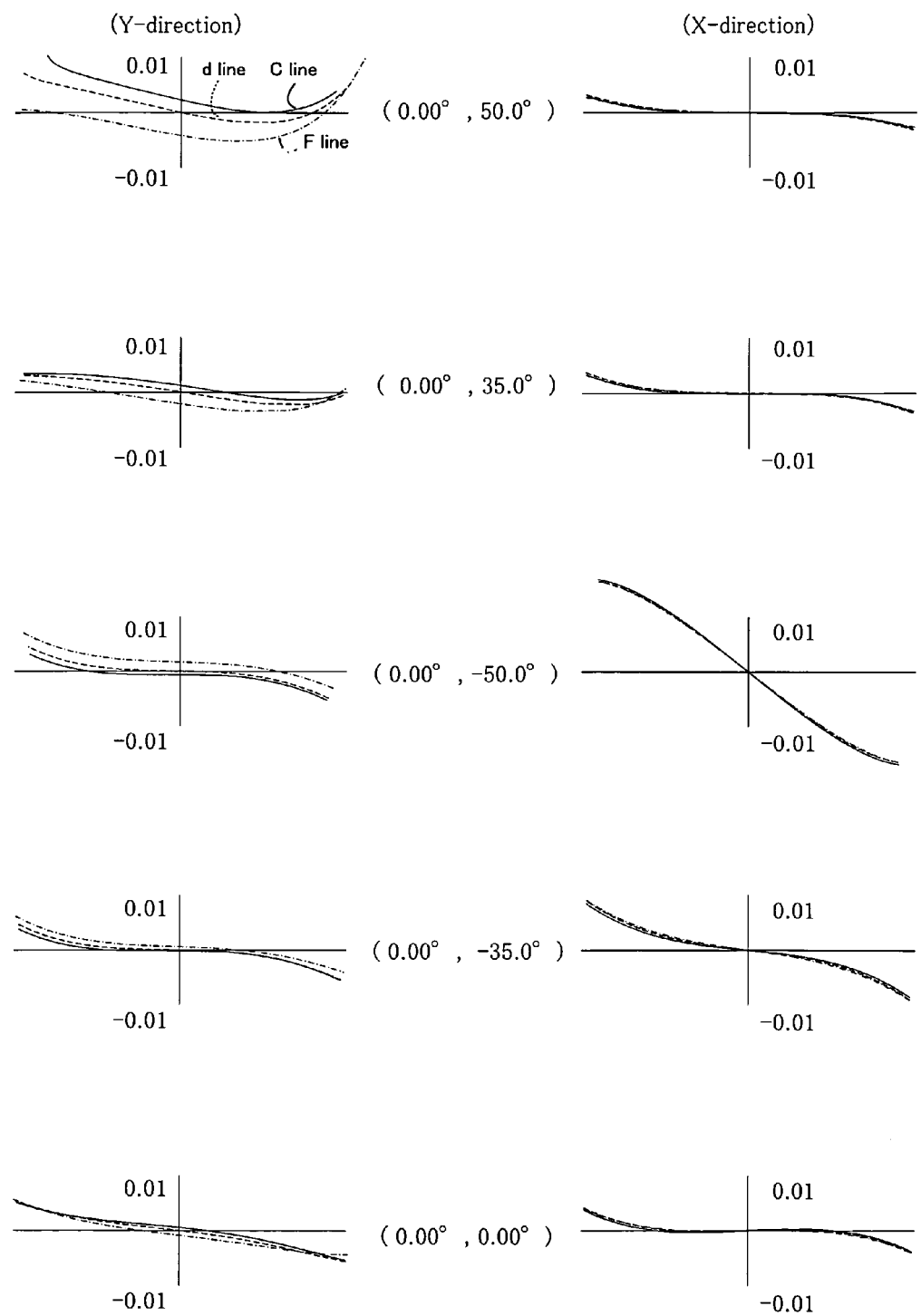
FIG. 7 is a schematic illustration of the transverse aberrations of the overall optical system of Example 2.
Figure 8:
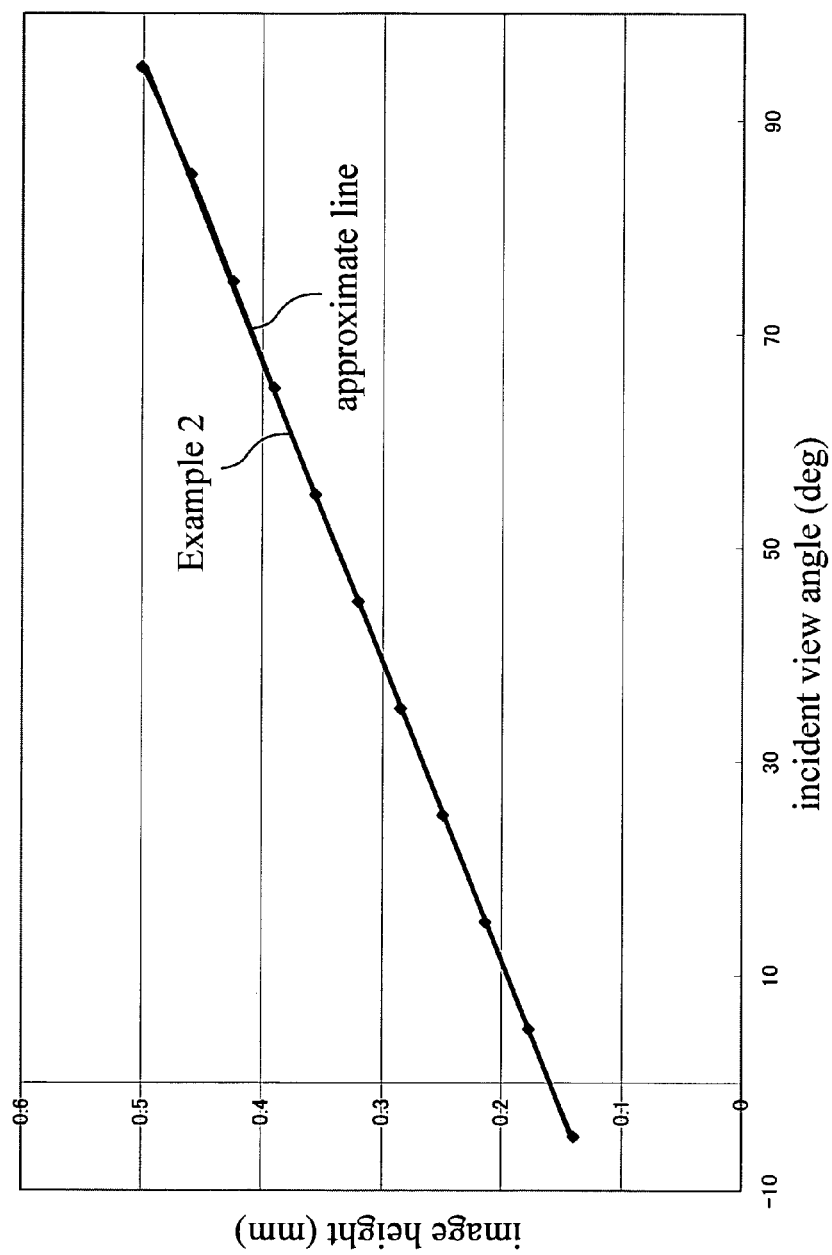
FIG. 8 is an F-θ graph of the overall optical system of Example 2.

FIG. 6 is a schematic cross-sectional view of the optical system 1 of Example 2 taken along the central axis 2 thereof. FIG. 7 is a schematic illustration of the transverse aberrations of the overall optical system of this example. FIG. 8 is a graph indicating the relationship between the view angle and the image height (F-θ diagram).

In this example, none of the transmissive surfaces and the reflective surfaces of the transparent medium, which is concentric with and rotationally symmetric relative to the central axis 2 of the optical system 1 and has a refractive index greater than 1, is shared in the optical path and hence all the surfaces are different surfaces.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The back group Gb includes a first group G1, a second group G2 and a third group G3.

The parallel flat plate arranged near the aperture S typically operates as a filter F. The parallel flat plate near the image plane 5 is typically a cover glass C for the imaging element.

The front group Gf is formed by a transparent medium L1 that is rotationally symmetric relative to the central axis 2 and has a refractive index greater than 1. The transparent medium L1 has a first transmissive surface 11 that is arranged vis-a-vis the object surface and formed by a toric surface at the external side relative to the central axis 2, a first reflective surface 12 that is formed by an extended rotary free curved surface in the inside of the transparent medium L1 and has negative power, a second reflective surface 13 that is formed by an extended rotary free curved surface in the inside of the transparent medium L1 at the opposite side to the image plane 5 relative to the first reflective surface 12 and has positive power and a second transmissive surface 14 that is formed by an aspheric surface at the image plane 5 side relative to the second reflective surface 13 and has negative power.

The back group Gb has a first group that is formed by a cemented lens of a negative meniscus lens L2 with its concave surface directed to the image plane 5 and a double convex positive lens L3, a second group that is formed by a double convex positive lens L4 and a third group that is formed by a cemented lens of a double convex positive lens L5 and a double concave negative lens L6.

The first group is formed by a cemented lens of a negative meniscus lens L2 with its convex surface directed to the object surface 3 and a double convex positive lens L3 and has a third transmissive surface 21, a cementing surface 23 arranged at the image plane 5 side relative to the third transmissive surface 21 and a fourth transmissive surface 31 arranged at the image plane 5 side relative to the cementing surface 23.

The second group is formed by a double convex positive lens L4 and has a fifth transmissive surface 41 and a six transmissive surface 42 arranged at the image plane 5 side relative to the fifth transmissive surface 41.

The third group is formed by a cemented lens of a double convex positive lens L5 and a double concave negative lens 6 and has a seventh transmissive surface 51, a cementing surface 56 arranged at the image plane 5 side relative to the seventh transmissive surface 51 and an eighth transmissive surface 61 arranged at the image plane 5 side relative to the cementing surface 56.

The optical system 1 forms an optical path A. As for the optical path A, the flux of light entering it from the object surface 3 of the optical system 1 proceeds sequentially by way of the front group Gf and the back group Gb and forms an annular image off the central axis 2 of the image plane 5 extending perpendicularly relative to the central axis 2.

The flux of light entering the optical system 1 to proceed along the optical path A goes into the transparent medium L1 of the front group Gf by way of the first transmissive surface 11 so as to be reflected by the first reflective surface 12 to the opposite side to the image plane 5 and then by the second reflective surface 13 to the image plane 5 side to form a subsequently Z-shaped optical path before going out from the transparent medium L1 by way of the second transmissive surface 14.

Subsequently, the flux of light goes into the cemented lens of the negative meniscus lens L2 and the double convex positive lens L3 of the first group of the back group Gb at the opposite side relative to the central axis 2 by way of the aperture S that is arranged between the front group Gf and the back group Gb coaxially with the central axis 2 to operate as a stop and the third transmissive surface 21 and goes out from the fourth transmissive surface 31 by way of the cementing surface 23. Then, it goes into the double convex positive lens L4 of the second group by way of the fifth transmissive surface 41 and goes out from the sixth transmissive surface 42. Thereafter, it goes into the cemented lens of the double convex positive lens L5 and the double concave negative lens L6 of the third group by way of the seventh transmissive surface 51 and goes out from the eighth transmissive surface 61 by way of the cementing surface 56 to form an image at a radially predetermined position off the central axis 2 of the image plane 5.

The specifications of Example 2 are as follows.

| view angle | −5° to 95° |
|---|---|
| image size | ø0.28 to ø1.00 |
| F number | 1.81 |

Figure 9:
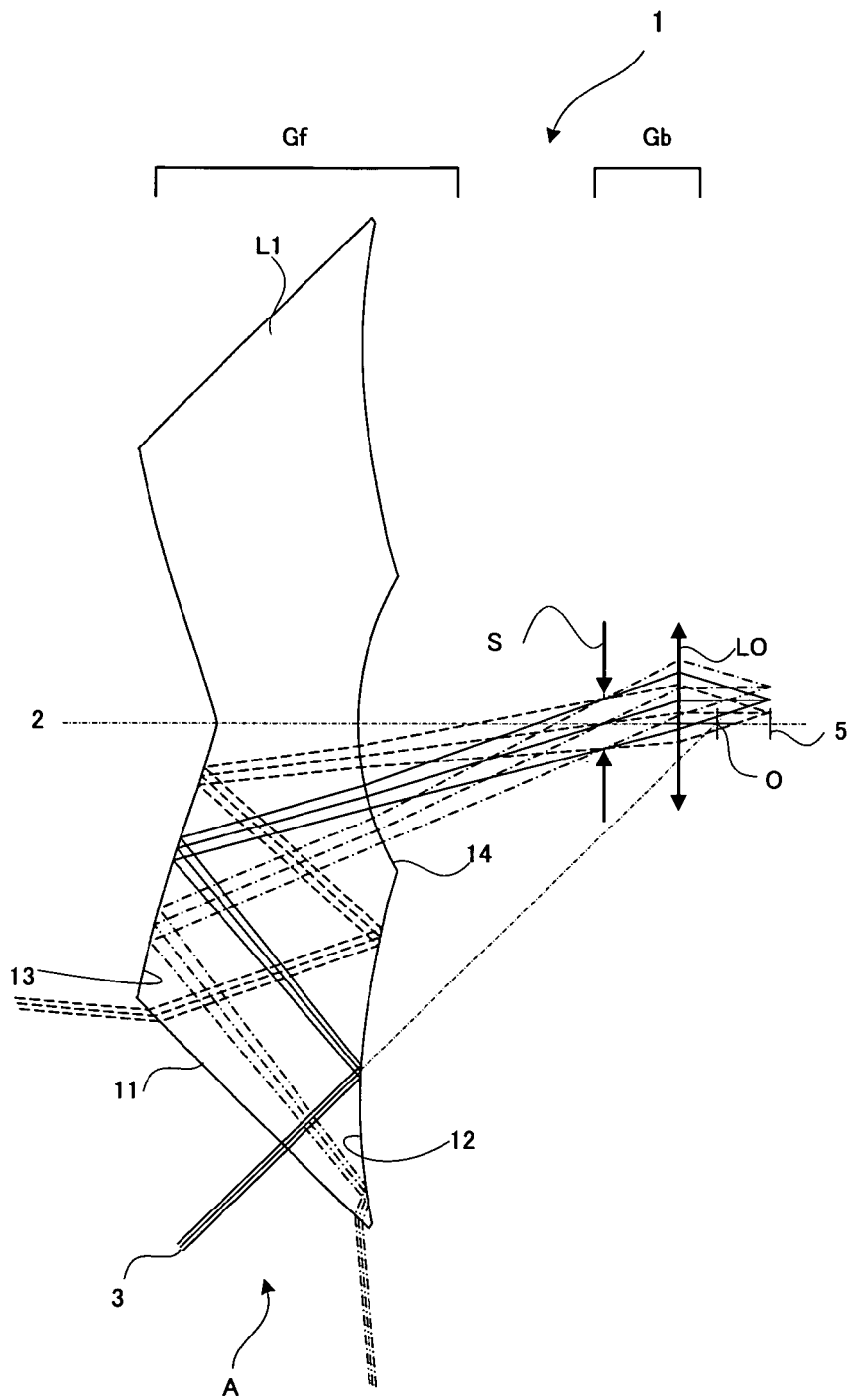
FIG. 9 is a schematic cross-sectional view of the optical system of Example 3 of the present invention taken along the central axis thereof.
Figure 10:
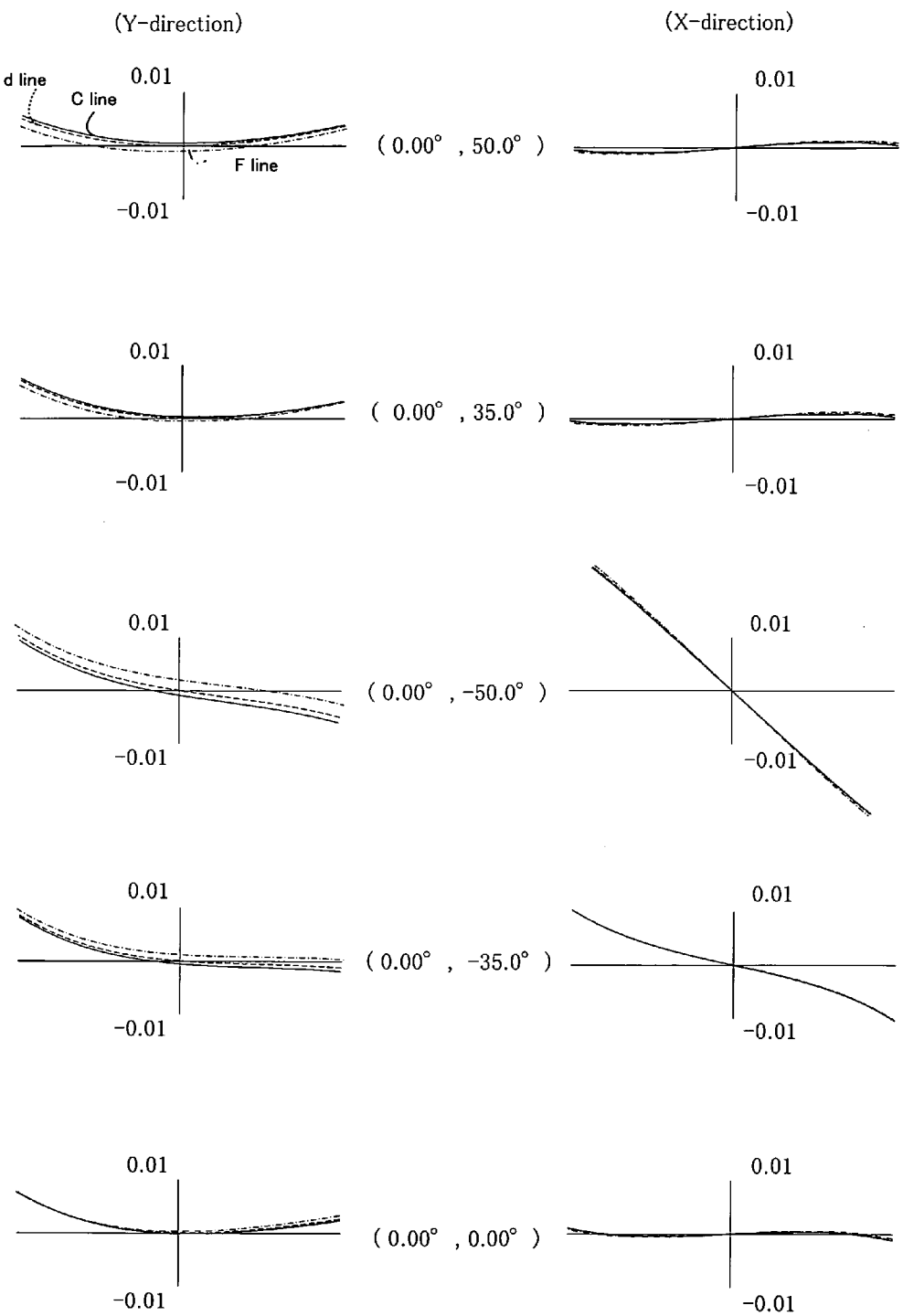
FIG. 10 is a schematic illustration of the transverse aberrations of the overall optical system of Example 3.
Figure 11:
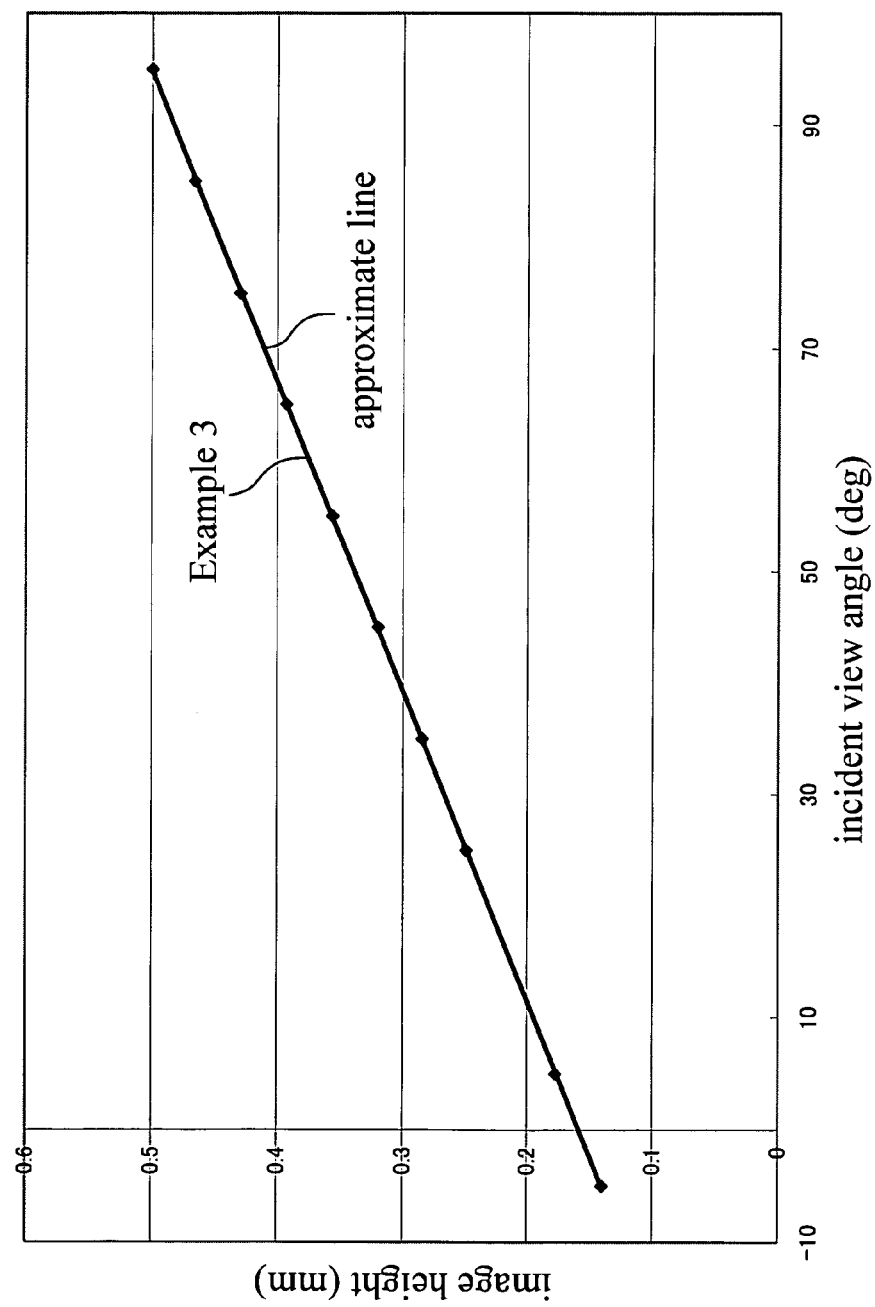
FIG. 11 is an F-θ graph of the overall optical system of Example 3.

FIG. 9 is a schematic cross-sectional view of the optical system 1 of Example 3 taken along the central axis 2 thereof. FIG. 10 is a schematic illustration of the transverse aberrations of the overall optical system of this example. FIG. 11 is a graph indicating the relationship between the view angle and the image height (F-θ diagram).

In this example, none of the transmissive surfaces and the reflective surfaces of the transparent medium, which is concentric with and rotationally symmetric relative to the central axis 2 of the optical system 1 and has a refractive index greater than 1, is shared in the optical path and hence all the surfaces are different surfaces. The optical system is formed as an attachment optical system to be fitted to the front end of an existing optical system. In the drawings, the arrows indicate an ideal lens L0.

The optical system 1 includes a front group Gf that is rotationally symmetric relative to the central axis 2, a back group Gb that is made of an ideal lens L0 and an aperture S arranged between the front group Gf and the back group Gb so as to be coaxial with the central axis 2.

The front group Gf is formed by a transparent medium L1 that is rotationally symmetric relative to the central axis 2 and has a refractive index greater than 1. The transparent medium L1 has a first transmissive surface 11 that is arranged vis-a-vis the object surface and formed by a toric surface at the external side relative to the central axis 2, a first reflective surface 12 that is formed by an extended rotary free curved surface in the inside of the transparent medium L2 and has negative power, a second reflective surface 13 that is formed by an extended rotary free curved surface in the inside of the transparent medium L2 at the opposite side to the image plane 5 relative to the first reflective surface 12 and has positive power and a second transmissive surface 14 that is formed by a spherical surface at the image plane 5 side relative to the second reflective surface 13 and has negative power.

The back group Gb is an ideal lens L0.

The optical system 1 forms an optical path A. As for the optical path A, the flux of light entering it from the object surface 3 of the optical system 1 proceeds sequentially by way of the front group Gf and the back group Gb and forms an annular image off the central axis 2 of the image plane 5 extending perpendicularly relative to the central axis 2.

The flux of light entering the optical system 1 to proceed along the optical path A goes into the transparent medium L1 of the front group Gf by way of the first transmissive surface 11 so as to be reflected by the first reflective surface 12 to the opposite side to the image plane 5 and then by the second reflective surface 13 to the image plane 5 side to form a subsequently Z-shaped optical path before going out from the transparent medium L1 by way of the second transmissive surface 14.

Subsequently, the flux of light proceeds by way of the aperture S that is arranged between the front group Gf and the back group Gb coaxially with the central axis 2 to operate as a stop and the ideal lens L0 of the back group Gb to form an image at a radially predetermined position off the central axis 2 of the image plane 5.

The specifications of Example 3 are as follows.

| | |
|---|---|
| view angle | −5° to 95° |
| image size | ø0.28 to ø1.00 |
| F number | 1.81 |
| f of ideal lens | 1.00 |

Figure 12:
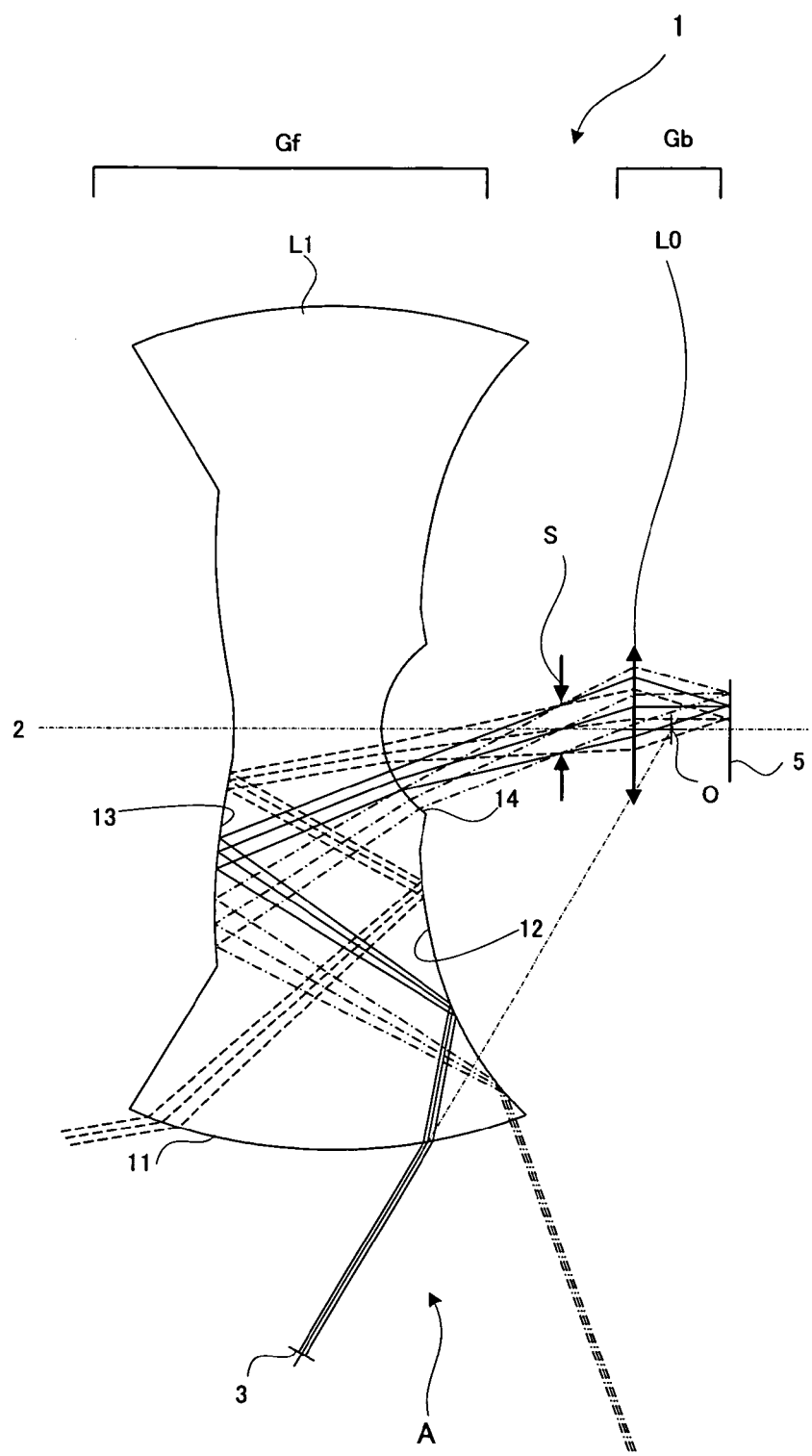
FIG. 12 is a schematic cross-sectional view of the optical system of Example 4 of the present invention taken along the central axis thereof.
Figure 13:
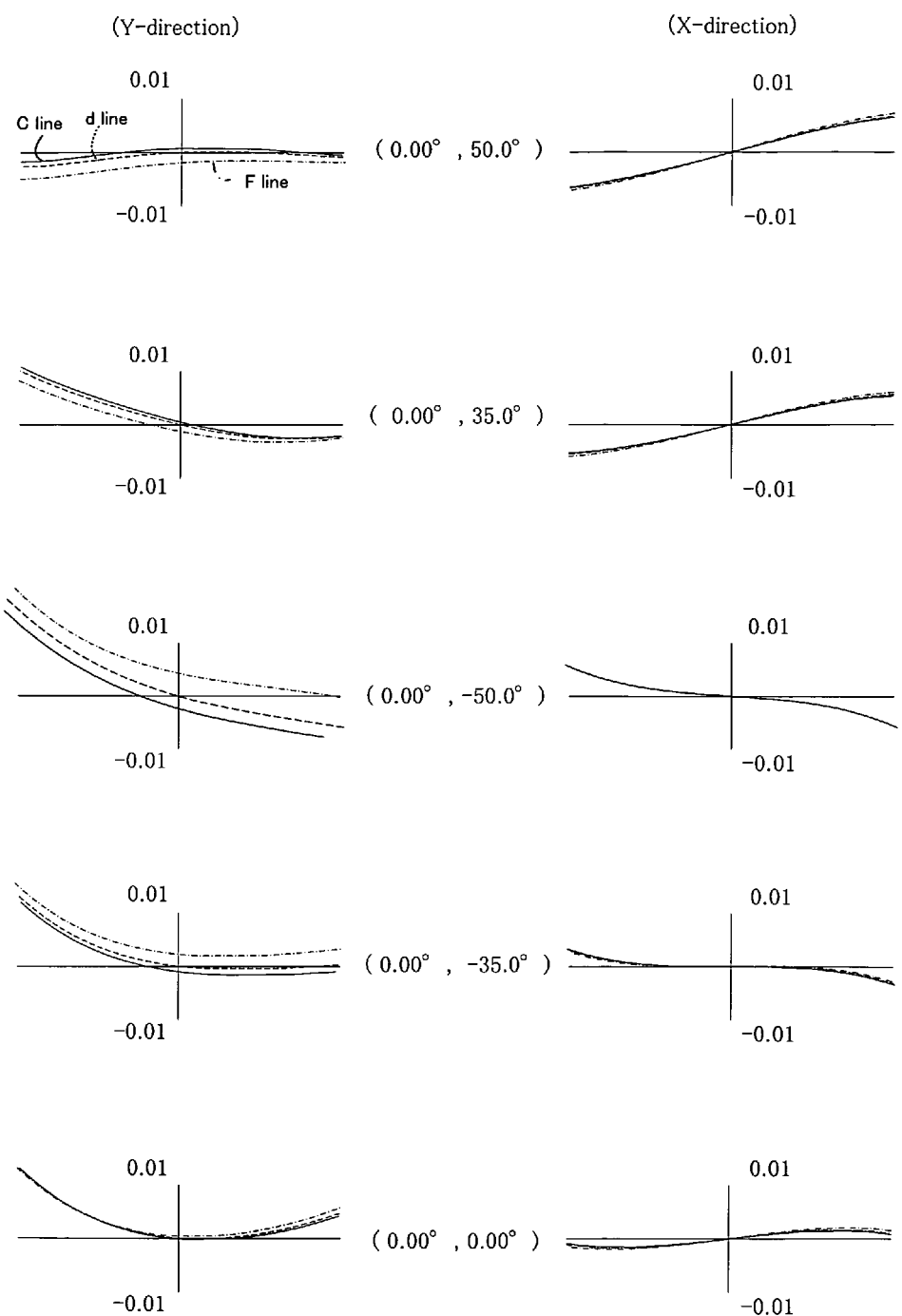
FIG. 13 is a schematic illustration of the transverse aberrations of the overall optical system of Example 4.
Figure 14:
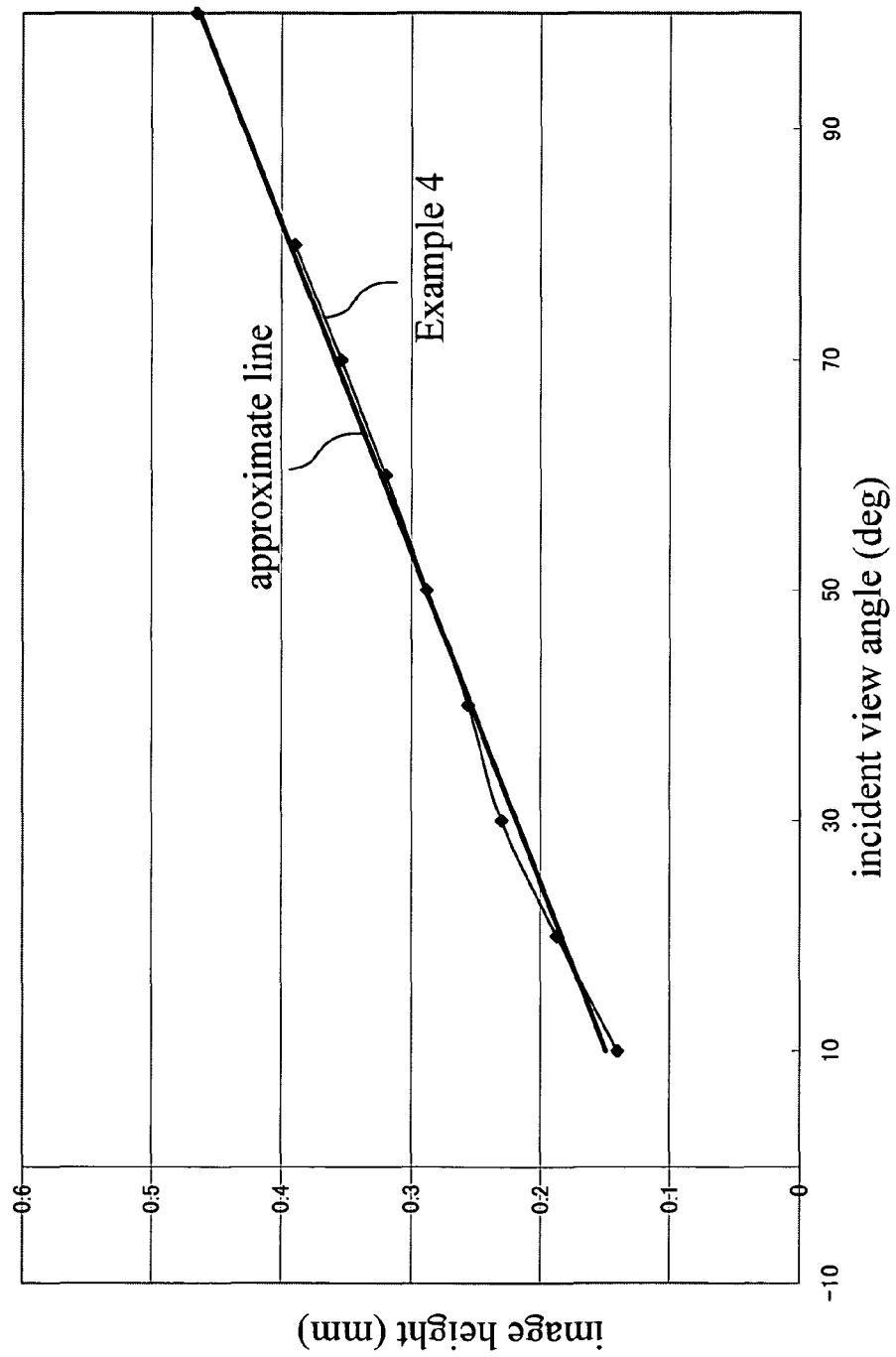
FIG. 14 is an F-θ graph of the overall optical system of Example 4.

FIG. 12 is a schematic cross-sectional view of the optical system 1 of Example 4 taken along the central axis 2 thereof. FIG. 13 is a schematic illustration of the transverse aberrations of the overall optical system of this example. FIG. 14 is a graph indicating the relationship between the view angle and the image height (F-θ diagram).

In this example, none of the transmissive surfaces and the reflective surfaces of the transparent medium, which is concentric with and rotationally symmetric relative to the central axis 2 of the optical system 1 and has a refractive index greater than 1, is shared in the optical path and hence all the surfaces are different surfaces. The optical system is formed as an attachment optical system to be fitted to the front end of an existing optical system. In the drawings, the arrows indicate an ideal lens L0.

The optical system 1 includes a front group Gf that is rotationally symmetric relative to the central axis 2, a back group Gb that is made of an ideal lens L0 and an aperture S arranged between the front group Gf and the back group Gb so as to be coaxial with the central axis 2.

The front group Gf is formed by a transparent medium L1 that is rotationally symmetric relative to the central axis 2 and has a refractive index greater than 1. The transparent medium L1 has a first transmissive surface 11 that is arranged vis-a-vis the object surface and formed by a toric surface at the external side relative to the central axis 2, a first reflective surface 12 that is formed by an extended rotary free curved surface in the inside of the transparent medium L1 and has negative power, a second reflective surface 13 that is formed by an extended rotary free curved surface in the inside of the transparent medium L2 at the opposite side to the image plane 5 relative to the first reflective surface 12 and has positive power and a second transmissive surface 14 that is formed by a spherical surface at the image plane 5 side relative to the second reflective surface 13 and has negative power.

The back group Gb is an ideal lens L0.

The optical system 1 forms an optical path A. As for the optical path A, the flux of light entering it from the object surface 3 of the optical system 1 proceeds sequentially by way of the front group Gf and the back group Gb and forms an annular image off the central axis 2 of the image plane 5 extending perpendicularly relative to the central axis 2.

The flux of light entering the optical system 1 to proceed along the optical path A goes into the transparent medium L1 of the front group Gf by way of the first transmissive surface 11 so as to be reflected by the first reflective surface 12 to the opposite side to the image plane 5 and then by the second reflective surface 13 to the image plane 5 side to form a subsequently Z-shaped optical path before going out from the transparent medium L1 by way of the second transmissive surface 14.

Subsequently, the flux of light proceeds by way of the aperture S that is arranged between the front group Gf and the back group Gb coaxially with the central axis 2 to operate as a stop and the ideal lens L0 of the back group Gb to form an image at a radially predetermined position off the central axis 2 of the image plane 5.

The specifications of Example 4 are as follows.

| | |
|---|---|
| view angle | 10° to 110° |
| image size | ø0.28 to ø1.00 |
| F number | 1.85 |
| f of ideal lens | 1.00 |

Some of the parameters of the above-described Examples 1 through 4 are listed below. In the table indicated below, "ASS" denotes an aspheric surface and "ERFS" denotes an extended rotary free curved surface, while "RE" denotes a reflective surface.

EXAMPLE 1

| Surface number | Radius of curvature | Plane gap | Eccentricity | Refractive index | Abbe number |
|---|---|---|---|---|---|
| Object surface | ∞ | ∞ | eccentricity (1) | | |
| 1 | ERFS [1] | | eccentricity (2) | 1.8348 | 42.7 |
| 2 | ERFS [2] (RE) | | eccentricity (3) | 1.8348 | 42.7 |
| 3 | ERFS [3] (RE) | | eccentricity (4) | 1.8348 | 42.7 |
| 4 | 4.56 | | eccentricity (5) | | |
| 5 | ∞ (Stop) | 1.00 | eccentricity (6) | | |
| 6 | Ideal lens | 1.12 | | | |
| Image surface | ∞ | | | | |

| ERFS [1] | |
|---|---|
| RY | −98.62 |
| θ | 45.00 |
| R | −8.26 |

| ERFS [2] | |
|---|---|
| RY | 12.09 |
| θ | 2.09 |
| R | −6.41 |

| ERFS [3] | |
|---|---|
| RY | 25.09 |
| θ | −10.83 |
| R | −2.94 |

| eccentricity [1] | | | | | |
|---|---|---|---|---|---|
| X | 0.00 | Y | 0.00 | Z | 0.00 |
| α | 45.00 | β | 0.00 | γ | 0.00 |

| eccentricity [2] | | | | | |
|---|---|---|---|---|---|
| X | 0.00 | Y | −8.26 | Z | −8.26 |
| α | 45.00 | β | 0.00 | γ | 0.00 |

| eccentricity [3] | | | | | |
|---|---|---|---|---|---|
| X | 0.00 | Y | −6.41 | Z | −6.41 |
| α | 2.09 | β | 0.00 | γ | 0.00 |

| eccentricity [4] | | | | | |
|---|---|---|---|---|---|
| X | 0.00 | Y | −2.94 | Z | −10.43 |
| α | −10.83 | β | 0.00 | γ | 0.00 |

| eccentricity [5] | | | | | |
|---|---|---|---|---|---|
| X | 0.00 | Y | 0.00 | Z | −6.99 |
| α | 0.00 | β | 0.00 | γ | 0.00 |

| eccentricity [6] | | | | | |
|---|---|---|---|---|---|
| X | 0.00 | Y | 0.00 | Z | −1.50 |
| α | 0.00 | β | 0.00 | γ | 0.00 |

EXAMPLE 2

| Surface number | Radius of curvature | Plane gap | Eccentricity | Refractive index | Abbe number |
|---|---|---|---|---|---|
| Object surface | ∞ | ∞ | eccentricity (1) | | |
| 1 | ERFS [1] | | eccentricity (2) | 1.8348 | 42.7 |
| 2 | ERFS [2] (RE) | | eccentricity (3) | 1.8348 | 42.7 |
| 3 | ERFS [3] (RE) | | eccentricity (4) | 1.8348 | 42.7 |
| 4 | ASS [1] | | eccentricity (5) | | |
| 5 | ∞ | 0.50 | eccentricity (6) | 1.5163 | 64.1 |
| 6 | ∞ (Stop) | 0.10 | | | |
| 7 | 3.94 | 0.30 | | 1.8467 | 23.8 |
| 8 | 1.40 | 1.00 | | 1.7407 | 44.9 |
| 9 | −2.67 | 0.10 | | | |
| 10 | 3.04 | 0.60 | | 1.6204 | 60.3 |
| 11 | −5.34 | 0.10 | | | |
| 12 | 1.79 | 1.00 | | 1.6204 | 60.3 |
| 13 | −1.32 | 0.30 | | 1.8467 | 23.8 |
| 14 | 9.16 | 0.30 | | | |
| 15 | ∞ | 0.40 | | 1.5163 | 64.1 |
| 16 | ∞ | 0.10 | | | |
| Image surface | ∞ | | | | |

ERFS [1]

| | |
|---|---|
| RY | −145.30 |
| θ | 45.00 |
| R | −6.84 |

ERFS [2]

| | | | |
|---|---|---|---|
| RY | 16.86 | | |
| θ | 2.40 | | |
| R | −5.14 | | |
| C4 | −1.1325E−03 | C5 | −6.7639E−04 |

ERFS [3]

| | | | |
|---|---|---|---|
| RY | 63.33 | | |
| θ | −9.74 | | |
| R | −1.68 | | |
| C4 | −7.4594E−03 | C5 | −2.6870E−03 |

ASS [1]

| | |
|---|---|
| R | 0.68 |
| k | −1.3647E−01 | eccentricity [1]

| X | 0.00 | Y | 0.00 | Z | 0.00 |
|---|---|---|---|---|---|
| α | 0.00 | β | 0.00 | γ | 0.00 | eccentricity [2]

| X | 0.00 | Y | 0.00 | Z | −6.84 |
|---|---|---|---|---|---|
| α | 0.00 | β | 0.00 | γ | 0.00 | eccentricity [3]

| X | 0.00 | Y | 0.00 | Z | −5.14 |
|---|---|---|---|---|---|
| α | 0.00 | β | 0.00 | γ | 0.00 | eccentricity [4]

| X | 0.00 | Y | 0.00 | Z | −9.24 |
|---|---|---|---|---|---|
| α | 0.00 | β | 0.00 | γ | 0.00 | eccentricity [5]

| X | 0.00 | Y | 0.00 | Z | −5.83 |
|---|---|---|---|---|---|
| α | 0.00 | β | 0.00 | γ | 0.00 | eccentricity [6]

| X | 0.00 | Y | 0.00 | Z | −4.48 |
|---|---|---|---|---|---|
| α | 0.00 | β | 0.00 | γ | 0.00 |

EXAMPLE 3

| Surface number | Radius of curvature | Plane gap | Eccentricity | Refractive index | Abbe number |
|---|---|---|---|---|---|
| Object surface | ∞ | ∞ | eccentricity (1) | | |
| 1 | ERFS [1] | | eccentricity (2) | 1.8348 | 42.7 |
| 2 | ERFS [2] (RE) | | eccentricity (3) | 1.8348 | 42.7 |
| 3 | ERFS [3] (RE) | | eccentricity (4) | 1.8348 | 42.7 |
| 4 | 4.05 | | eccentricity (5) | | |
| 5 | ∞ (Stop) | 1.00 | eccentricity (6) | | |
| 6 | Ideal lens | 1.20 | | | |
| Image surface | ∞ | | | | |

ERFS [1]

| | |
|---|---|
| RY | 135.56 |
| θ | 45.00 |
| R | −5.70 |

ERFS [2]

| | | | |
|---|---|---|---|
| RY | 8.30 | | |
| θ | −2.95 | | |
| R | −4.70 | | |
| C4 | −4.0540E−03 | C5 | −1.5338E−03 |

ERFS [3]

| | | | |
|---|---|---|---|
| RY | 28.47 | | |
| θ | −17.50 | | |
| R | −1.70 | | |
| C4 | −8.0029E−03 | C5 | −1.9714E−03 | eccentricity [1]

| X | 0.00 | Y | 0.00 | Z | 0.00 |
|---|---|---|---|---|---|
| α | 45.00 | β | 0.00 | γ | 0.00 | eccentricity [2]

| X | 0.00 | Y | 0.00 | Z | −5.70 |
|---|---|---|---|---|---|
| α | 0.00 | β | 0.00 | γ | 0.00 | eccentricity [3]

| X | 0.00 | Y | 0.00 | Z | −4.70 |
|---|---|---|---|---|---|
| α | 0.00 | β | 0.00 | γ | 0.00 | eccentricity [4]

| X | 0.00 | Y | 0.00 | Z | −7.13 |
|---|---|---|---|---|---|
| α | 0.00 | β | 0.00 | γ | 0.00 | eccentricity [5]

| X | 0.00 | Y | 0.00 | Z | −4.74 |
|---|---|---|---|---|---|
| α | 0.00 | β | 0.00 | γ | 0.00 | eccentricity [6]

| X | 0.00 | Y | 0.00 | Z | −1.50 |
|---|---|---|---|---|---|
| α | 0.00 | β | 0.00 | γ | 0.00 |

EXAMPLE 4

| Surface number | Radius of curvature | Plane gap | Eccentricity | Refractive index | Abbe number |
|---|---|---|---|---|---|
| Object surface | ∞ | ∞ | eccentricity (1) | | |
| 1 | ERFS [1] | | eccentricity (2) | 1.8348 | 42.7 |
| 2 | ERFS [2] (RE) | | eccentricity (3) | 1.8348 | 42.7 |
| 3 | ERFS [3] (RE) | | eccentricity (4) | 1.8348 | 42.7 |
| 4 | 1.45 | | eccentricity (5) | | |
| 5 | ∞ (Stop) | 1.00 | eccentricity (6) | | |
| 6 | Ideal lens | 1.29 | | | |

-continued

| Image ∞ surface | | | | |
|---|---|---|---|---|
| ERFS [1] | | | | |
| RY | 7.21 | | | |
| θ | 100.26 | | | |
| R | −5.73 | | | |
| ERFS [2] | | | | |
| RY | 4.93 | | | |
| θ | 22.65 | | | |
| R | −3.89 | | | |
| C4 | −8.8849E−03 | C5 | −2.0610E−04 | |
| ERFS [3] | | | | |
| RY | 9.10 | | | |
| θ | −5.82 | | | |
| R | −1.71 | | | |
| C4 | −1.0337E−02 | C5 | −3.3607E−03 | |
| eccentricity [1] | | | | |
| X | 0.00 | Y | 0.00 | Z | 0.00 |
| α | 60.00 | β | 0.00 | γ | 0.00 |
| eccentricity [2] | | | | |
| X | 0.00 | Y | 0.00 | Z | −3.31 |
| α | 0.00 | β | 0.00 | γ | 0.00 |
| eccentricity [3] | | | | |
| X | 0.00 | Y | 0.00 | Z | −2.97 |
| α | 0.00 | β | 0.00 | γ | 0.00 |
| eccentricity [4] | | | | |
| X | 0.00 | Y | 0.00 | Z | −6.15 |
| α | 0.00 | β | 0.00 | γ | 0.00 |
| eccentricity [5] | | | | |
| X | 0.00 | Y | 0.00 | Z | −3.95 |
| α | 0.00 | β | 0.00 | γ | 0.00 |
| eccentricity [6] | | | | |
| X | 0.00 | Y | 0.00 | Z | −1.50 |
| α | 0.00 | β | 0.00 | γ | 0.00 |

Examples 1 through 4 represent the following values for t, d, θ1, θ2, ts, d1 and β, where t is the thickness of the optical element as measured along the axis of rotational symmetry, d is the external dimension, θ1 is the angle of incidence of the central principal ray of light at the first reflective surface, θ2 is the angle of incidence of the central principal ray of light at the second reflective surface ts is the length of the gap between the first reflective surface and the aperture and d1 is the diameter of the first reflective surface and β is the angular magnification of the view angle at the meridional cross section (exiting view angle/entering view angle in the air).

| | Example 1 | Example 2 | Example 3 | Example 4 |
|---|---|---|---|---|
| t | 3.5 | 5.0 | 4.8 | 3.26 |
| d | 21.0 | 18.0 | 13.6 | 12.0 |
| d/t | 4.4 | 3.6 | 3.6 | 3.7 |
| θ1 | 42.9 | 42.6 | 47.9 | 57.0 |
| θ2 | 30.0 | 30.5 | 33.4 | 28.6 |
| ts | 4.7 | 0.6 | 3.0 | 6.0 |
| d1 | 17.8 | 17.4 | 13.0 | 10.2 |
| d1/ts | 3.8 | 29.0 | 4.3 | 1.7 |
| β | 0.18 | 0.15 | 0.18 | 0.18 |

While each of the transmissive surfaces and the reflective surfaces of the transparent medium that is concentric with and rotationally symmetric relative to the central axis 2 of the optical system 1 and has a refractive index greater than 1 is designed as an extended rotary free curved surface in each of the above describe examples, an extended rotary free curved surface is equivalent to a spherical surface when the extended rotary free curved surface is orthogonal to a rotationally symmetric surface and does not involve any term of higher degree.

While each of the reflective surfaces and the refractive surfaces of the front group Gf is designed as an extended rotary free curved surface that is formed by rotating a line segment of an arbitrary shape around the central axis 2 and does not have the surface vertex on the central axis 2, it may be replaced by an arbitrary curved surface.

Additionally, in an optical system according to the present invention, the inclination of the image plane 5 that arises due to eccentricity and the pupil aberration that arises when the stop is back-projected are corrected by using a formula that involve one or more than one odd-number-th degree terms for the formula for defining a line segment of an arbitrary shape for forming a rotationally symmetric surface.

An image with an omni-directional view angle of 360° can be picked up and projected by using a transparent medium that is rotationally symmetric around the central axis 2 of the front group Gf for the purpose of the present invention. However, an image with a view angle of 180°, 120°, 240° or some other angle may be picked up or projected by cutting the transparent medium along a cross section that includes the central axis 2 to a half, one-third, two-third or the like.

An optical system according to the present invention is described above as an image pickup or observation optical system that can obtain an image with an omni-directional (all-around) view angle of 360° including the vertex and the central axis (axis of rotational symmetry) 2 vertically directed, the present invention is not limited to image pickup optical systems and observation optical systems and an optical system according to the present invention can be used as a projection optical system for projecting an image with an omni-directional (all-around) view angle of 360° including the vertex where the optical path is followed reversely. Furthermore, an optical system according to the present invention can be used as an omni-directional optical system of an endoscope or an intra-canal observation apparatus.

FIG. 15 is a schematic illustration of an exemplar positional arrangement of an image of an optical system according to Present Examples and an imaging element. In FIG. 15, (a) is an example of using an imaging element with an aspect ratio of 16:9. When no vertically long image is used, the dimension of the imaging element 50 is preferably made equal to the distance between the left margin and the right margin of the image A1 of the optical path A. In FIG. 15, (b) is an example of using an imaging element 50 with an aspect ratio of 4:3 and making the dimension of the imaging element 50 where no vertically long image is used as in (a) of FIG. 15. In FIG. 15, (c) is an example of using an imaging element 50 with an aspect ratio of 4:3 and making the dimension of the imaging element 50 agree with that of the image A1 of the optical path A. With this arrangement, all the images A1 of the optical path A can be entirely picked up.

Figure 16:
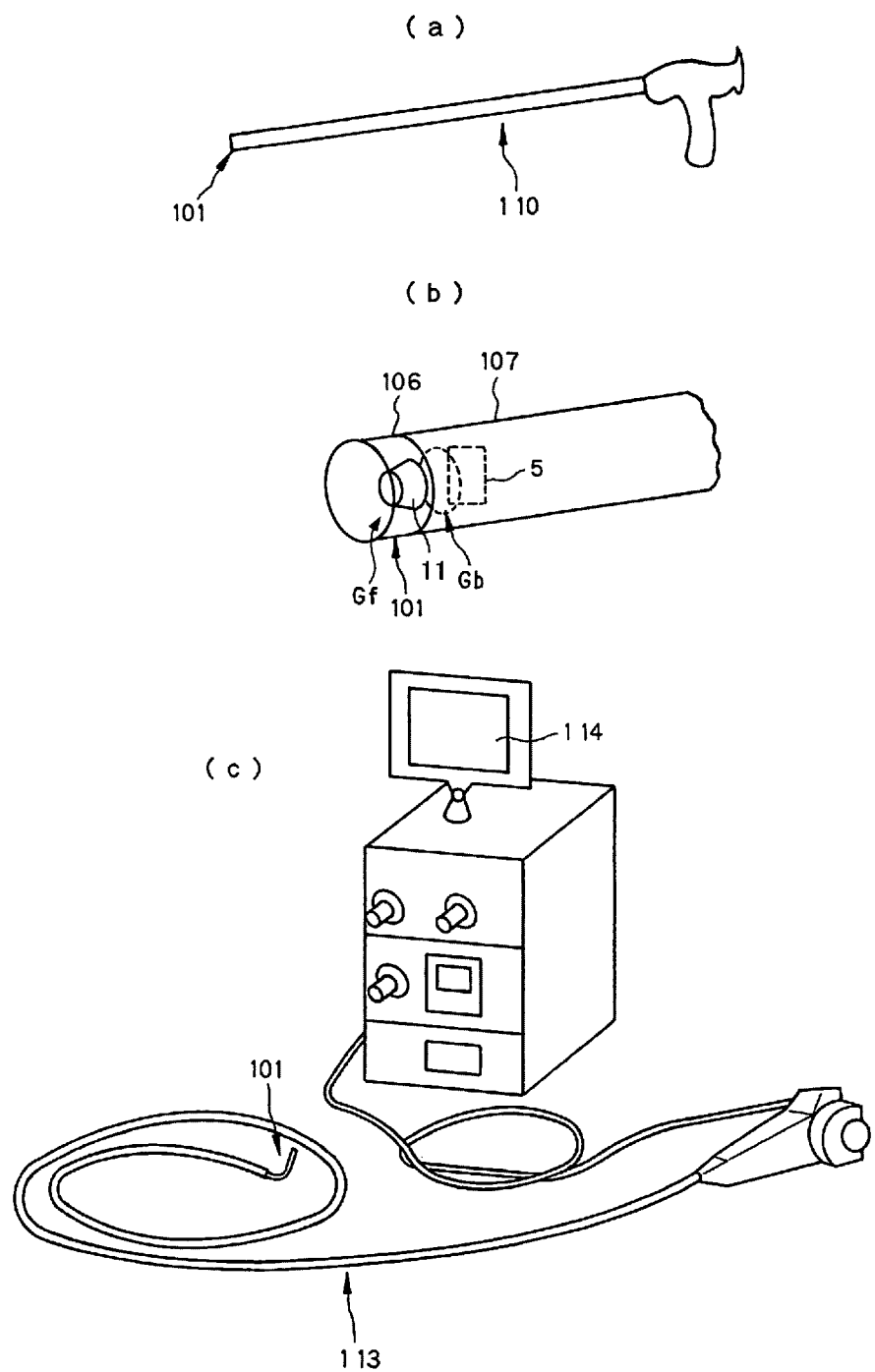
FIG. 16 is a schematic illustration of an example of using an optical system according to the present invention as an image pickup optical system at the front end of an endoscope.

Now, examples of using an image pickup optical system 101 and those of using a projection optical system 102 will be described below as applications of an optical system 1 according to the present invention. FIG. 16 is a schematic illustration of an example of using an image pickup optical system 101 according to the present invention as an image pickup optical system at the front end of an endoscope. In FIG. 16, (a) illustrates an example of mounting an image pickup optical system according to the invention to the front end 101 of a rigid endoscope 110 and picking up and observing a 360° omni-directional image. In FIG. 16, (b) schematically illustrates the configuration of the front end thereof. A flare stop 107 that is formed by a casing having a peripherally extending slit-like aperture 106 is arranged at the incident surface 11 of the front group Gf of a panoramic image pickup optical system 101 according to the present invention in order to prevent flare from entering. In FIG. 16, (c) illustrates an example of similarly mounting a panoramic image pickup optical system 101 according to the invention to the front end of a soft electronic endoscope 113 and displaying a picked up image on a display apparatus 114 after subjecting it to image processing.

Figure 17:
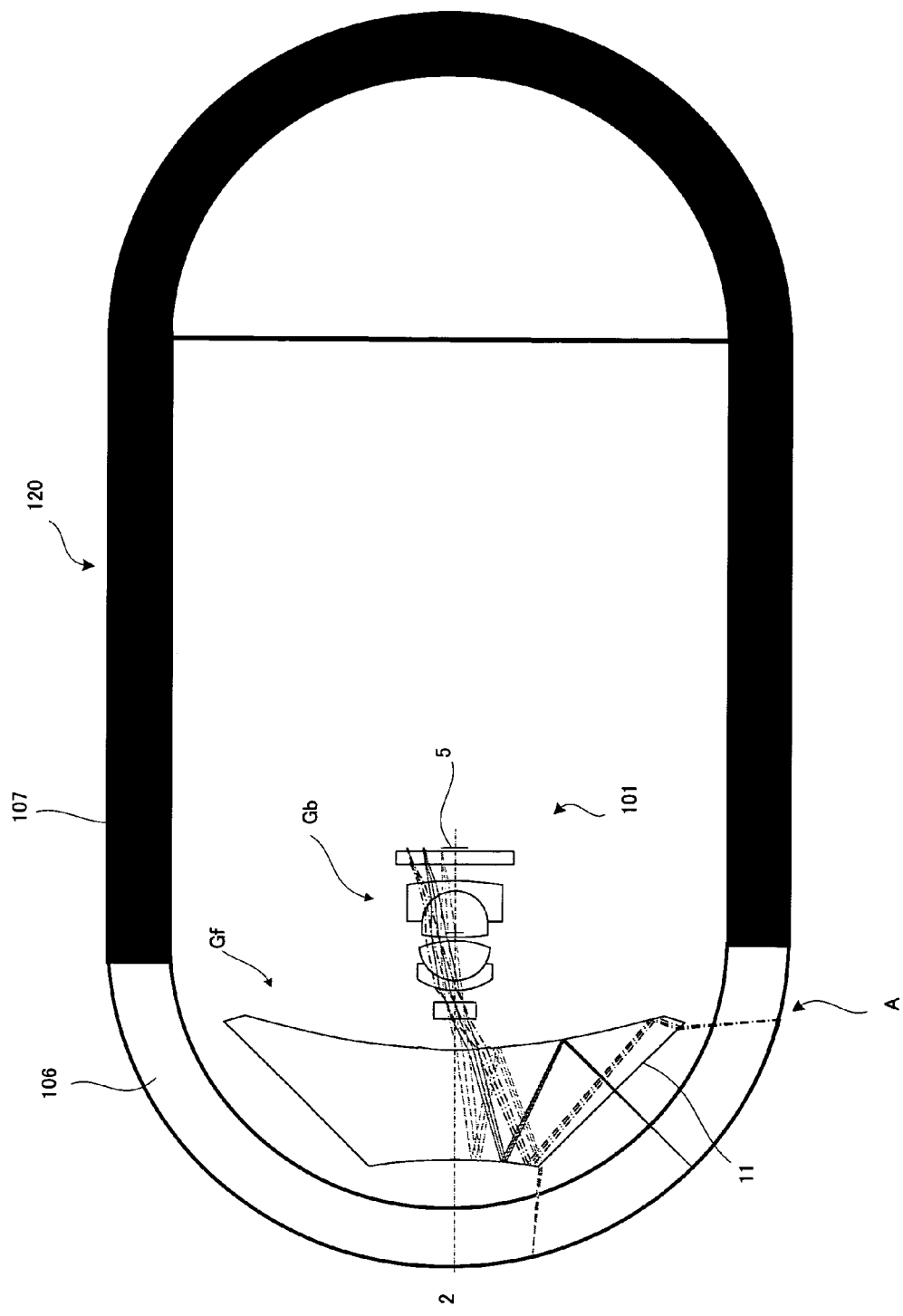
FIG. 17 is a schematic illustration of an example of using an optical system according to the present invention as an image pickup optical system of a capsule endoscope.

FIG. 17 is schematic illustrations of Example 1 of mounting an image pickup optical system 101 to a capsule endoscope 120 and picking up and observing a 360° omni-directional image. A flare stop 107 is formed at a casing having a aperture 106 around the front side and first transmissive surface 11 of the front group Gf at the optical path A of an image pickup optical system 101 according to the present invention in order to prevent flare from entering.

As illustrated in FIGS. 16 and 17, an image of any of various parts can be picked up for observation from behind an image pickup optical system 101 according to the present invention when it is applied to an endoscope so that the part can be shot from various angles in order to pick up images therefore for the purpose of observation, although no such images can be picked up according to the conventional art.

In FIG. 18, (a) illustrates an example of fitting an image pickup optical system 101 according to the present invention to the front side of an automobile 130, processing the images picked up by each of the image pickup optical systems 101 fitted to the automobile including the above-described one to correct distortions and displaying the images simultaneously. In FIG. 18, (b) illustrates an example of fitting a plurality of image pickup optical systems 101 according to the present invention respectively to various parts of an automobile 130 including corners and the top of the pole at the head of the automobile 130, processing the images picked up by each of the image pickup optical systems 101 to correct distortions and displaying the images simultaneously. The dimension of each of the imaging elements 50 is preferably made equal to the distance between the left margin and the right margin of the image A1 of the corresponding optical path A as described above by referring to (a) of FIG. 15 to obtain a horizontally broad view.

Figure 19:
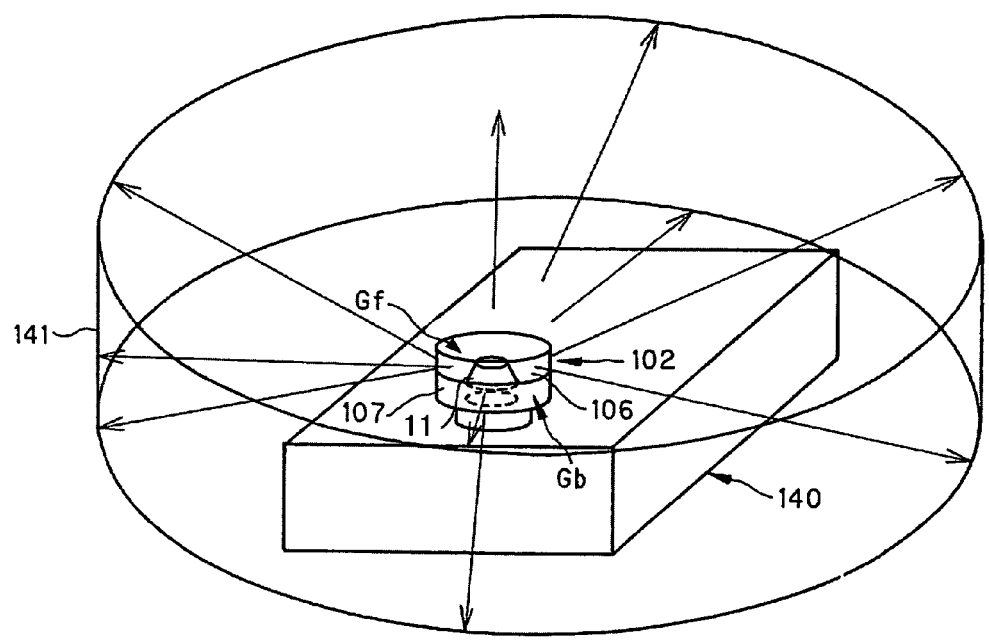
FIG. 19 is a schematic illustration of an example of using an optical system according to the present invention as a projection optical system of a projection apparatus.

FIG. 19 is a schematic illustration of an example of using a projection optical system 102 according to the present invention as a projection optical system of a projection apparatus 140. The picked up panoramic image is displayed on a display element arranged on the image plane 5 of the optical system and then a 360° omni-directional image is projected and displayed on a screen 141 arranged 360° omni-directionally by way of a projection optical system 102.

Figure 20:
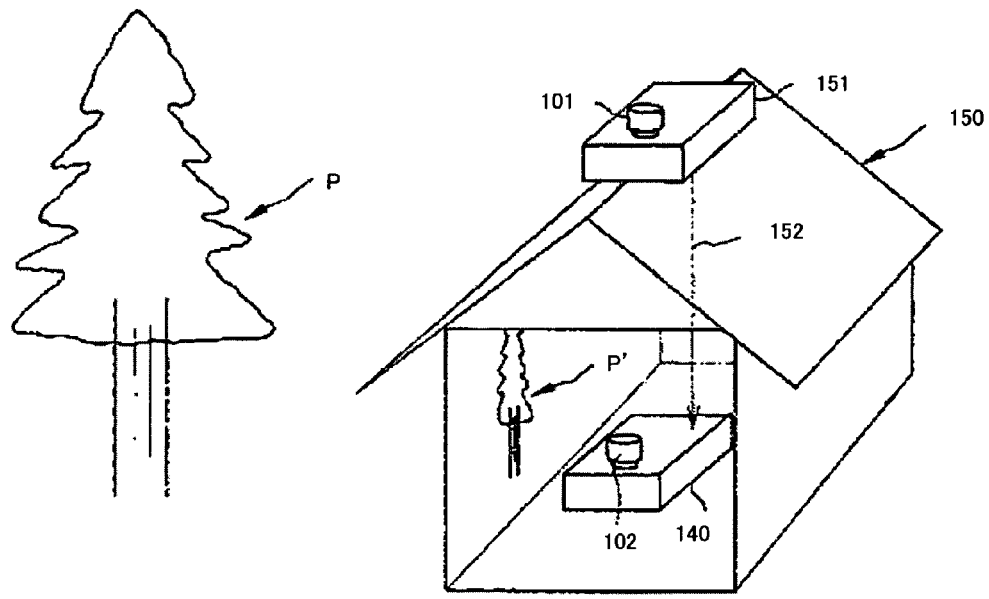
FIG. 20 is a schematic illustration of an example of using an optical system according to the present invention as an image pickup optical system for picking up an image of an outdoor object.

In the example of FIG. 20, an image pickup apparatus 151 including an image pickup optical system 101 according to the present invention is arranged at the outside of a building 150, while a projection apparatus 140 including another image pickup optical system 101 according to the present invention is arranged in the inside of the building and connected to the image pickup apparatus 151, and the image picked up by the image pickup apparatus 151 is sent to the projection apparatus 140 by way of an electric wire 152. An 360° omni-directional image of an outdoor object P is picked up by the image pickup apparatus 151 by way of the image pickup optical system 101 and the video signal of the picked up image is sent to the projection apparatus 140 by way of the electric wire 152 so that the image is displayed on the display element arranged on the image plane and then an enlarged image P' of the object P is projected and displayed on a wall in the building by way of the projection optical system 102.

The invention claimed is:

1. An optical element that is made of a transparent medium rotationally symmetric relative to the central axis with a refractive index greater than 1, wherein
the transparent medium has a first transmissive surface, a first reflective surface, a second reflective surface arranged at an opposite side to the image plane relative to the first reflective surface and a second transmissive surface arranged at the image plane side relative to the second reflective surface and that the flux of light entering the transparent medium goes thereinto by way of the first transmissive surface so as to be reflected to the opposite side to the image plane by the first reflective surface and then to the image plane side by the second reflective surface to form an optical path before going out from the transparent medium at the image plane side byway of the second transmissive surface in the order of forward ray tracing.

2. The optical element according to claim 1, wherein the optical path is formed a substantially Z-shaped optical path.

3. The optical element according to claim 1, wherein the optical path is formed only at a side relative to the central axis.

4. The optical element according to claim 1, wherein the second transmissive surface is arranged near the central axis and the first reflective surface and the second reflective surface are arranged in a peripheral part thereof, while the first transmissive surface is arranged at the outermost periphery thereof.

5. The optical element according to claim 1, wherein each of the first reflective surface and the second reflective surface is formed by a toric surface.

6. The optical element according to claim 1, wherein at least either the first reflective surface and the second reflective surface has a total reflection effect.

7. The optical element according to claim 1, wherein at least either the first reflective surface and the second reflective surface is formed by an extended rotary free curved surface formed by rotating a line segment of arbitrary shape having no plane of symmetry around the central axis.

8. The optical element according to claim 1, wherein at least one of the surfaces that the transparent medium has is formed by an extended rotary free curved surface formed by rotating a line segment of arbitrary shape including one or more than one odd-number-th degree terms.

9. An optical system having an optical element according to claim 1, wherein
the system includes a front group, a back group arranged at the image plane side relative to the front group and an aperture arranged between the front group and the back group and that the optical element is arranged in the front group to form an image of an object arranged so as to surround the central axis or project an image of the object in a radial direction from the central axis.

10. The optical system according to claim 9, wherein the system forms an image of an annular object around the central axis in a plane orthogonal relative to the central axis.

11. The optical system according to claim 9, wherein the second reflective surface is arranged with the concave surface thereof directed to the aperture.

12. The optical system according to claim 9, wherein the second transmissive surface is arranged with the concave surface thereof directed to the aperture.

13. The optical system according to claim 9, wherein the system does not form any intermediate image on the optical path.

14. The optical system according to claim 9, wherein the system satisfies the condition of $$1 < d/t \qquad (1),$$

where t is the thickness of the optical element as measured in the direction of the axis of rotational symmetry and d is the external dimension of the optical element.

15. The optical system according to claim 9, wherein the system satisfies the condition of $$3 < d/t \qquad (1\text{-}1),$$

where t is the thickness of the optical element as measured in the direction of the axis of rotational symmetry and d is the external dimension of the optical element.

16. The optical system according to claim 9, wherein the system satisfies the condition of $$20 < \theta 2 < 40 \qquad (2),$$

where θ1 is the angle of incidence of the central principal ray of light on the first reflective surface and θ2 is the angle of incidence of the central principal ray of light on the first reflective surface of the optical element.

17. The optical system according to claim 9, wherein the first reflective surface is arranged at the opposite side to the image plane relative to the aperture.

18. The optical system according to claim 9, wherein the system satisfies the condition of $$0 < d1/ts < 1 \qquad (3)$$

where ts is the length of the gap between the first reflective surface and the aperture and d1 is the diameter of the first reflective surface of the optical element.

19. The optical system according to claim 9, wherein the system satisfies the condition of $$0.05 < \beta < 2 \qquad (4),$$

where β is the angular magnification of the view angle of the meridional cross section.

20. The optical system according to claim 9, wherein the system satisfies the condition of $$0.1 < \beta < 2 \qquad (4\text{-}1),$$

where β is the angular magnification of the view angle of the meridional cross section.

21. An endoscope characterized by being formed by using an optical system according to claim 9.

* * * * *